United States Patent [19]
Florkiewicz

[11] Patent Number: 5,891,855
[45] Date of Patent: Apr. 6, 1999

[54] INHIBITORS OF LEADERLESS PROTEIN EXPORT

[75] Inventor: Robert Z. Florkiewicz, Ramona, Calif.

[73] Assignee: The Scripps Research Institute, La Jolla, Calif.

[21] Appl. No.: 599,895

[22] Filed: Feb. 12, 1996

[51] Int. Cl.$^6$ .................... A61K 31/705; A01N 45/00; C07K 1/00

[52] U.S. Cl. .................... 514/26; 514/25; 514/27; 514/28; 514/29; 514/30; 514/31; 435/184; 530/351; 530/396; 530/399

[58] Field of Search .................... 514/25, 26, 27, 514/28, 29, 30, 31; 435/184; 530/351, 396, 399

[56] References Cited

U.S. PATENT DOCUMENTS 5,545,623  8/1996  Matsumori .................... 514/26
5,627,195  5/1997  Hu .................... 514/321

FOREIGN PATENT DOCUMENTS

WO 96/04921  2/1996  WIPO .

OTHER PUBLICATIONS

Cooper and Barondes, "Evidence for Export of a Muscle Lectin from Cytosol to Extracellular Matrix and for a Novel Secretory Mechanism," *Journal of Cell Biology 110*: 1681–1691, 1990.

Florkiewicz et al., "Multiple Forms of bFGF: Differential Nuclear and Cell Surface Localizaton," *Growth Factors 4*:265–275, 1991.

Florkiewicz et al., "Quantitative Export of FGF–2 Occurs Through an Alternative, Energy–Dependent, Non–ER/Golgi Pathway," *Journal of Cellular Physiology 162*: 388–399, 1995.

Jackson et al., "Heat shock induces the release of fibroblast growth factor 1 from NIH 3T3 cells," *Proc. Natl. Acad. Sci. USA 89*: 10691–10695, 1992.

Jackson et al., "The Release of Fibroblast Growth Factor–1 from NIH 3T3 Cells In Response to Temperature Involves the Function of Cysteine Residues," *Journal of Biological Chemisty 270*(1): 33–36, 1995.

Mignatti et al., "Basic Fibroblast Growth Factor, a Protein Devoid of Secretory Signal Sequence, Is Released by Cells via a Pathway Independent of the Endoplasmic Reticulum–Golgi Complex," *Journal of Cellular Physiology 151*: 81–93, 1992.

Repke et al., "Potential suitablility of $NA^+/K^+$–transporting ATPase in pre–screens for anti–cancer agents," *Anti–Cancer Drug Design 10*: 177–187, 1995.

Rubartelli et al., "A novel secretory pathway for interleukin–1β, a protein lacking a signal sequence," *EMBO Journal 9*(5): 1503–1510, 1990.

Rubartelli et al., "Secretion of Thioredoxin by Normal and Neoplastic Cells through a Leaderless Secretory Pathway," *Journal of Biological Chemistry 267*(34): 24161–24164, 1992.

Rubartelli et al., "Post–Translational Regulation of Interleukin 1β Secretion," *Cytokine 5*(2): 117–124, 1993.

Siders and Mizel, "Interleukin–1β Secretion. A Possilbe Multistep Process that is Regulated in a Cell Type–Specific Manner," *Journal of Biological Chemistry 270*(27): 16258–16264, 1995.

Katahira et al. *Chemotherapy* Jul. 1991, 39(7), 678–686.

Callard et al. "The Cytokine FactsBook" Academic Press Limited, London, 1994, pp. 31–38.

Brooks, D., "Protein Secretion by the Rat Epididymis Can Be Selectively Modified in Vitro by Local Anesthetics, Glucose Deprivation, Dinitrophenol, Ouabain and Ionophores," *J. Androl. 5*: 351–360, 1984.

Crutchely and Smariga, "Monovalent Cation Dependence of Tissue Plasminogen Activator Synthesis by HeLa Cells," *Journal of Biological Chemistry 262*(7): 3017–3021, 1987.

*Primary Examiner*—Kathleen K. Fonda
*Attorney, Agent, or Firm*—Seed & Berry LLP

[57] ABSTRACT

This invention provides methods of inhibiting the export of a leaderless protein from a cell by contacting the cell with a cardiac glycoside or aglycone derivative. Leaderless proteins include FGF-1, FGF-2, IL,-1α, IL-1β and factor XIIIa. These methods are useful in treatment of conditions, including tumors and diabetes.

17 Claims, 6 Drawing Sheets

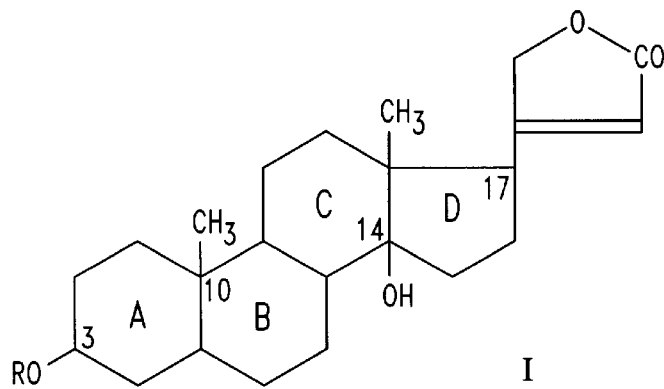

*Lanatoside A* (Digilanide A): R = (digitoxose)$_3$-D- glucose + acetyl.
 (Naturally occurring in *Digitalis lanata, Digitalis ferruginea*.)
*Desacetyllanatoside A* (Purpuren Glycoside A): R = (digitoxose)$_3$-D-glucose.
 (Naturally occurring in *Digitalis purpurea* or from Lanatoside A by hydrolysis with mild alkali.)
*Acetyl Digitoxin*: R = (digitoxose)$_3$+acetyl. (Derived from Lanatoside A by enzymatic action.)
*Digitoxin*: R = (digitoxose)$_3$. (In *Digitalis purpurea* and *Digitalis lanata* by enzymatic breakdoown of Purpuren Glycoside A or Lanatoside A.)

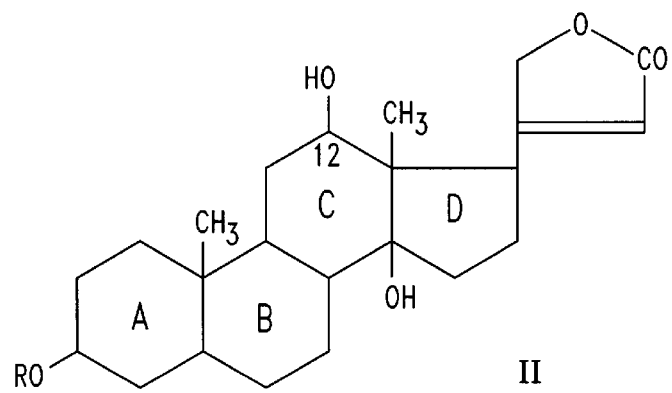

*Lanatoside C*: R = (digitoxose)$_3$-D- glucose + acetyl.
 (Naturally occurring in *Digitalis lanata*.)
*Desacetyllanatoside C*: R = (digitoxose)$_3$-D- glucose.
 (Derived from Lanatoside C by hydrolysis with mild alkali.)
*Digoxin* R = (digitoxose)$_3$. (In *Digitalis lanata* by enzymatic breakdoown of Lanatoside C.)

*Fig. 1A*

*Strophanthoside*: R = cymarose-β-D glucose-α-D glucose (In *Strophanthus Kombe*.)
K-*Strophanthin*: R = cymarose-β-D-glucose (In *Strophanthus Kombe*.)

*Ouabain* (g-strophanthin) R = L-rhamnose (In *Strophanthus gratus*.)

*Scillaren A*: R = L-rhamnose-D-glucose (In *Scilla maritima*.)
*Proscillaridin A*: R = L-rhamnose (*Scilla maritima*.)

INHIBITORS OF LEADERLESS PROTEIN EXPORT

Support for this invention was provided in part by government funding through NIH DK18811. The government may have certain rights in this invention.

TECHNICAL FIELD

The present invention relates generally to inhibitors of leaderless protein export, and more specifically, to the use of cardiac glycosides and aglycone derivatives to inhibit export of leaderless proteins into extracellular spaces.

BACKGROUND OF THE INVENTION

Many proteins exert an effect on cell growth, differentiation, and inflammation through signal transduction, mediated by binding to a cell surface receptor. Yet other proteins such as factors that initiate or are necessary for blood clot formation, act enzymatically in blood. While these actions are generally part of normal processes, under certain circumstances, it may be desirable to limit or inhibit the action of certain proteins and the effects of subsequent signaling. For example, tumor growth promoted by a growth factor, such as bFGF acting on melanoma cells, is deleterious and often leads to fatalities.

Approaches to inhibit specific proteins have concentrated primarily on interfering with protein-substrate or protein-receptor interactions. Typically, this involves using an antibody or other molecule that competitively binds the protein, by administration of competitors for receptor binding, or by protease digestion of the protein. An alternative approach, not generally pursued, is to reduce the level of the protein by inhibiting its expression at a transcriptional or translational level. Methods of reducing protein levels by inhibiting the transcription or translation of the protein have been difficult to achieve because of inherent problems of inhibiting the specific expression of one or a few proteins.

The discovery that certain proteins, such as growth factors, mediators of inflammation, and mediators of blood clotting, are exported through a nonclassical secretory pathway allows the development of specific inhibitors for these proteins. These proteins are identified by their lack of a hydrophobic leader sequence that mediates secretion by the classical Golgi/ER pathway. These proteins are believed to be exported from a cell by exocytosis.

This invention provides inhibitors of the export of these leaderless proteins, allowing control of undesired proliferation and inflammation, as well as other related advantages.

SUMMARY OF THE INVENTION

The present invention generally provides methods of inhibiting the export of a leaderless protein from a cell expressing the protein. In one aspect of the invention, export is inhibited by contacting a cell expressing the protein with a cardiac glycoside. In certain embodiments, the cardiac glycoside is selected from the group consisting of digoxin, strophanthin K, digitoxin, lanatoside A and ouabain. Preferably the cardiac glycoside is ouabain or digoxin.

In another aspect of the invention, methods of inhibiting the export of a leaderless protein from a cell expressing the protein by contacting the cell with an aglycone derivative of a cardiac glycoside are provided. In certain embodiments, the aglycone derivative is selected from the group consisting of digoxigenin, digitoxigenin and uzarigenin. Preferably the aglycone derivative is digoxigenin.

In other aspects, methods are provided for inhibiting the export of FGF-2 from a cell expressing FGF-2, comprising contacting the cell with a cardiac glycoside or aglycone derivative of a cardiac glycoside. In yet other aspects, methods of treating an FGF-mediated pathophysiological condition in a patient are provided, comprising administering a therapeutically effective dosage of a cardiac glycoside or aglycone derivative of a cardiac glycoside, thereby reducing the amount of FGF-2 that is exported. In certain embodiments, the pathophysiological condition is melanoma, ovarian carcinoma, teratocarcinoma or neuroblastoma.

In yet other aspects, methods are provided for inhibiting proliferation of a cell bearing an FGF receptor, comprising contacting the cell with a cardiac glycoside or an aglycone derivative of a cardiac glucoside. In still other aspects, methods are provided for treating complications of diabetes, comprising contacting a cell with an inhibiting amount of a cardiac glycoside or aglycone derivative.

Methods are also provided for inhibiting export of leaderless proteins, comprising treating cells with a compound selected from the group consisting of formula 1, formula 2, formula 3, formula 4, or formula 5.

These and other aspects of the present invention will become evident upon reference to the following detailed description and attached drawings. Various references are set forth below which describe in more detail certain procedures or compositions (e.g., plasmids, etc.). All of these references are incorporated by reference in their entirety.

DETAILED DESCRIPTION OF THE INVENTION

As an aid to understanding the invention, certain definitions are provided herein.

Figure 1B:
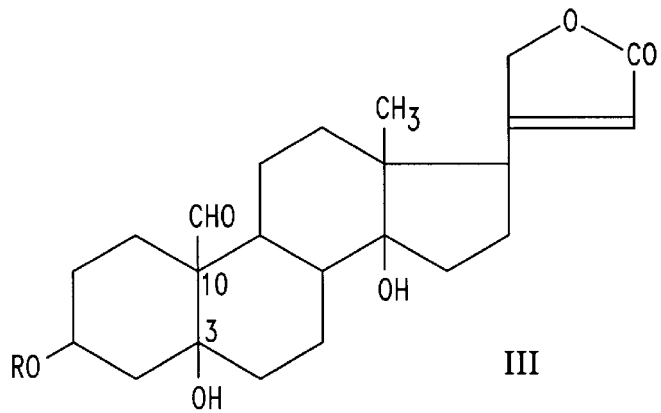
FIG. 1 is a drawing of the general structure of the aglycone nucleus of various cardiac glycosides.
Figure 1B:
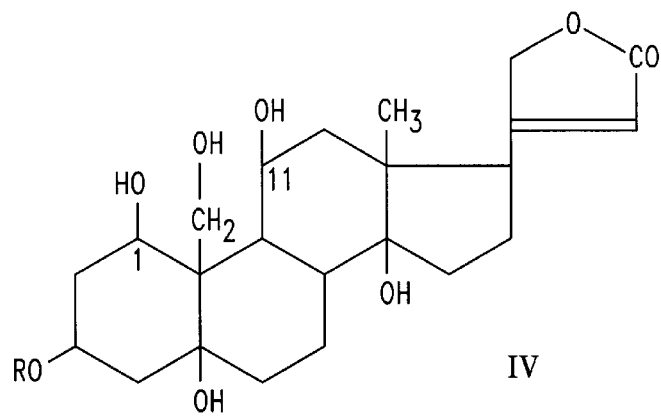
Figure 1B:
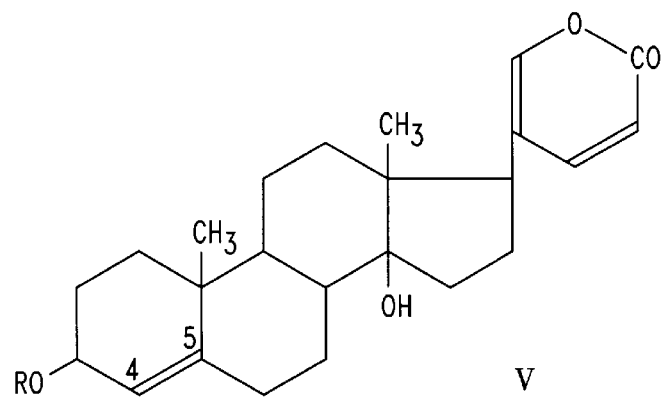

"Cardiac glycoside" refers to a group of compounds which are structurally related. Structurally, these compounds are derived from the cyclopentanoperhydro-phenanthrene nucleus characteristic of steroid compounds, have a five-membered unsaturated lactone ring or a six-membered doubly unsaturated lactone ring at C17 of ring D, a hydroxyl group at C3 in ring A for joining by an ether linkage to one or more sugar residues, and a hydroxy group at C14 (FIG. 1). The aglycone derivatives of cardiac glycosides have a similar structure, but lack the carbohydrates characteristic of the cardiac glycosides. These aglycone derivatives are also useful in the present invention. Representatives of this group are found in a number of botanical sources, as well as in mammals. (See, *A Survey of Cardiac Glycosides and Genins*, University of South Carolina Press, 1961.) The cardiac glycosides include ouabain-like/digoxin-like compounds that have been isolated from mammals (see, U.S. Pat. No. 4,780,314).

"Leaderless protein" refers to a protein or polypeptide that arrives in an extracellular environment but lacks a canonical leader sequence. A leader sequence mediates translocation into the ER and is recognized by signal recognition proteins (SRP). Proteins in the extracellular environment include secreted proteins found in extracellular spaces, as well as proteins that are membrane bound, but not an integral membrane protein. The prototypic leader sequence has an amino-terminal positively charged region, a central hydrophobic region, and a more polar carboxy-terminal region (see, von Heijne, *J. Membrane Biol.* 115:195–201, 1990). Leaderless proteins include FGF-1, FGF-2, interleukin 1α, interleukin 1β, vas deferens protein, platelet-derived endothelial cell growth factor, ciliary neurotrophic factor, thymosin, parathymosin, 14.5 kDa lectin (L 14), transglutaminase, thioredoxin-like protein, sciatic nerve growth-promoting activity, factor XIIIa, and int-2. Within the context of their invention, leaderless proteins include naturally occurring proteins as well as proteins that are engineered to lack a leader sequence, but are exported. The terms "signal sequence," "leader peptide," and "leader sequence" are used interchangeably herein.

"Export" of a protein refers to a metabolically active process of transporting a translated cellular product to the extracellular spaces or at the cell membrane by a mechanism other than by a leader sequence.

Leaderless Proteins

As noted above, leaderless proteins are proteins that arrive in the extracellular environment but lack a signal sequence which functions to mediate translocation of a protein into the ER by SRP recognition. Typically, these proteins are initially identified because their primary translation product lacks a canonical hydrophobic leader or signal sequence, which is usually located at the N-terminus of the primary translation product and is used in the transport process through the Golgi/ER. A leader sequence has three distinct domains: an amino-terminal positively charged region approximately 1–5 residues long; a central, hydrophobic region approximately 7–15 residues long; and a more polar carboxyterminal domain approximately 3–7 residues long (von Heijne, supra). The hydrophobic central region is critical.

Several leaderless proteins have been identified by virtue of their location in the extracellular environment, transport by a mechanism other than through the Golgi/ER, and lack of a leader sequence. Such proteins include IL-1α (SEQ ID NOS: 4, 5; precursor, mature forms), IL-1β (SEQ ID NOS: 6. 7; precursor; mature forms), FGF-1, FGF-2 (SFQ ID NO:1, 2; cDNA, 18 kD form), PD-ECGF (platelet-derived endothelial cell growth factor), CNTF (ciliary nutrotrophic factor), sciatic nerve growth-promoting activity, vas deferens protein, transglutaminase, L-14 lectin, factor XIIIa, thioredoxin-like protein (ADF), thymosin, parathymosin, and int-2.

Other leaderless proteins that are exported may be identified by a two-part assay: (1) identification of the protein in extracellular spaces, including at the membrane, and (2) brefeldin-resistant export. A preliminary assessment to identify candidate leaderless proteins may be made by inspection of the amino acid sequence of the primary translation product. Comparison of the amino-terminal sequence with other known leader sequences or identification of the prototypic pattern sequence, as described herein (von Hleijne, supra), provides a means to classify potential leaderless proteins. As discussed above, leader sequences are approximately 15–25 amino acids long and contain at minimum a central region of 7–15 hydrophobic residues, such as leucine, isoleucine, valine, glycine, phenylalanine, methionine, threonine, serine, proline, cysteine, alanine, tyrosine, and tryptophan. Any primary translation sequence of a protein that lacks such a sequence is a candidate for an exported leaderless protein.

As noted above, identification of a protein as a leaderless protein rests in the two-part assay, discovery of the protein in the extracellular environment and brefeldin-resistance.

The first assay is performed to detect the protein extracellularly. For this assay, test cells expressing a leaderless protein are necessary. Either the test cells may naturally produce the protein or preferably produce it from a transfected expression vector. For FGF-2 expression, COS cells are preferred for transfection. For expression of IL-1, p388D1 cells are preferred. Following expression, the protein is detected by any one of a variety of well known methods and procedures. Such methods include staining with antibodies in conjunction with flow cytometry, confocal microscopy, image analysis, immunoprecipitation of cell medium, Western blot of cell medium, ELISA, or bioassay. A preferred assay during initial screening is ELISA. Any candidate is confirmed by one of the other assays, preferably by immunoprecipitation of cell medium following metabolic labeling. Briefly, cells expressing the candidate leaderless protein are pulse labeled for 15 min with $^{35}$S-methionine and/or $^{35}$S-cysteine in methionine and/or cysteine free medium and chased in medium supplemented with excess methionine and/or cysteine. Medium fractions are collected and clarified by centrifugation in a microfuge. Lysis buffer containing 1% NP-40, 0.5% deoxycholate (DOC), 20 mM Tris, pH 7.5, 5 mM EDTA, 2 mM EGTA, 10 nM PMSF, 10 ng/ml aprotinin, 10 ng/ml leupeptin, and 10 ng/ml pepstatin is added to the clarified medium to inhibit proteases. Antibody to the candidate leaderless protein is added and following incubation in the cold, a precipitating second antibody or immunoglobulin binding protein, such as protein A-Sepharose® or GammaBind™-Sepharose® is added for further incubation. In parallel, as a control, a vector encoding a cytosolic protein is co-transfected and an antibody to a known cytosolic protein is used in immunoprecipitations. Immune complexes are pelleted and washed with ice-cold lysis buffer. Complexes are further washed with ice-cold IP buffer (0.15M NaCl, 10 mM Na-phosphate, pH 7.2, 1% DOC, 1% NP-40, 0.1% SDS). Immune complexes are eluted directly into SDS-gel sample buffer and electrophoresed in SDS-PAGE. The percentage of acrylamide will depend upon the molecular weight of the leaderless protein. The gel is processed for fluorography, dried and exposed to X-ray film. Proteins that are expressed at higher levels in medium as compared to the cytosolic protein control are tested for brefeldin resistant export.

Brefeldin-resistance is measured in cells expressing a leaderless protein as described above. Briefly, cells, such as COS-1 cells, are transfected with an expression vector directing expression of the leaderless protein, such as FGF-2. Approximately 2 days later, the transfected cells are metabolically pulse-labeled for 15 min with $^{35}$S-methionine and $^{35}$S-cysteine in met and cys free media. Label is removed, and the cells are further incubated in medium containing 15 μg/ml brefeldin A. For quantitation of FGF-2 export, 25 μg/ml heparin is added to the chase medium. Lack of statistically significant reduction in FGF-2 export indicates that protein export is brefeldin A resistant.

Inhibitors

As described above, cardiac glycosides and aglycones are inhibitors of the export of leaderless proteins. Cardiac glycosides and their aglycone derivatives are derived from the cyclopentanoperhydro-phenanthrene nucleus characteristic of steroid compounds (FIG. 1). At C17 of ring D, there is a five-membered unsaturated lactone ring or a six-membered doubly unsaturated lactone ring. At C3 on ring A, there is a hydroxyl group for joining to one or more sugar residues by an ether linkage, and at C14 there is a hydroxy group. In addition, other C atoms, such as C16, may have side groups. The sugar groups at C3 include monosaccharides, including glucose, rhamnose, cymarose, di-, tri, and polysaccharides, including cymarose-β-D-glucose, L-rhamnose-D-glucose, tridigitoxose, digitoxose$_3$-D-glucose, and the like, as well as saccharide derivatives. Aglycone derivatives have a similar structure to the cardiac glycosides, but lack the carbohydrate residue(s). However, other side groups may be substituted at the C3 position in aglycone derivatives. Together, cardiac glycosides and aglycone derivatives are classified as cardenolides.

Cardiac glycosides useful in the present invention include, but are not limited to, lanatoside A, desacetyllanatoside A, actyl digitoxin, digitoxin, lanatoside C, desacetyl-lanatoside C, digoxin, strophanthoside, K-strophanthin, ouabain, scillaren A, proscillaridin A, uzarin, digitoxose, gitoxin, strophanthidine-3β-digitoxoside, strophanthidin α-L-rhamnopyranoside, strophanthidol, oleandrin, acovenoside A, strophanthidine digilanobioside, strophanthidin-D-cymaroside, digitoxigenin-L-rhamnoside digitoxigenin theretoside, and the like. Aglycones include, but are not limited to, strophanthidin, digitoxigenin, uzarigenin, digoxigenin, digoxigenin 3,12-diacetate, gitoxigenin, gitoxigenin 3-acetate, gitoxigenin 3,16-diacetate, 16-acetyl gitoxigenin, acetyl strophanthidin, ouabagenin, 3-epidigoxigenin, and the like. Preferably the cardiac glycoside is ouabain, digoxin, or digitoxin. Most preferably, the cardiac glycoside is ouabain, and the aglycone derivative is strophanthidin.

Cardiac glycosides and aglycones may be purified from organisms, such as plants, or from human serum or urine. (see, for example, references in Merck Index, Tenth Edition; PCT application WO 91/17176; U.S. Pat. No. 4,780,314; Kelly et al., *Kidney Int'l* 30:723–729, 1986). The compounds may also be purchased commercially (e.g., Sigma Chemical Co., St. Louis, Mo.; Calbiochem, San Diego, Calif.).

Assays For Detecting Inhibition of Export of Leaderless Proteins

Cardiac glycoside or aglycone derivative inhibitors of export of leaderless proteins are identified by one of the assays described herein. Briefly, a cell expressing a leaderless protein is treated with the cardiac glycoside or aglycone derivative and the amount of leaderless protein detected as an extracellular protein is compared to the amount detected without treatment.

Within the context of the present invention, an inhibitor must meet three criteria: (1) it blocks export of a leaderless protein, (2) it does not block export of a secreted protein with a leader sequence, and (3) it does not promote expression of a cytosolic protein in the extracellular environment.

In any of the assays described herein, the test cell may express the leaderless protein either naturally or following introduction of a recombinant DNA molecule encoding the protein. Similarly, the expression of the secreted protein and cytosolic protein may be natural or following transfection of a vector encoding the protein. Recombinant expression of the leaderless protein is preferred. Any of the leaderless proteins described above, chimeric leaderless proteins (i.e., fusion of leaderless protein with another protein or protein fragment), or protein sequences engineered to lack a leader sequence may be used. Secreted proteins that are exported by virtue of a leader sequence are well known and include, human chorionic gonadatropin (HCGα) (SEQ ID NO:3), growth hormone, hepatocyte growth factor, transferrin, nerve growth factor, vascular endothelial growth factor, ovalbumin, and insulin-like growth factor. Similarly, cytosolic proteins are well known and include, neomycin, β-galactosidase, actin and other cytoskeletal proteins, enzymes, such as protein kinase A or C. The most useful cytosolic or secreted proteins are those that are readily measured in a convenient assay, such as ELISA. The three proteins may be co-expressed naturally or by transfection in the test cells, or transfected separately into host cells.

Merely by way of example, a construct containing the 18 kD isoform of FGF-2 is described. Plasmid 18dx encodes the 18 kD isoform of FGF-2, which was derived from the wild-type human FGF-2 cDNA as previously described (Florkiewicz and Sommer, *Proc. Natl. Acad. Sci. USA* 86:3978, 1989). The FGF-2 sequence was truncated 11 bp 5' of the ATG codon for the 18 kD isoform. Thus, only the 18 kD form may be expressed. A fragment containing the cDNA was inserted into pJC119, an SV-40 based expression vector. It will be apparent that other expression vectors may be interchangeably used and that the choice of the vector will depend in part upon the host cell to be transfected. FGF-2 cDNA was expressed in COS cells using an SV40-based expression vector. The vector, pJC119 (Sprague et al., *J. Virol.* 45:773, 1983), is an SV-40 based vector, which uses the SV-40 late promoter to control expression of the inserted gene. COS cells were chosen because they normally express very low levels of FGF-2 and, as such, possess the appropriate cellular machinery for export of this leaderless protein.

Other leaderless proteins described above may be used in constructs in place of FGF-2. DNA molecules encoding these proteins may be obtained by conventional methods, such as library screening, PCR amplification and cloning, or obtained from the ATCC/NIH repository of human and mouse DNA probes. Nucleotide sequences of these proteins are generally available from Genbank, and EMBL databases or publications.

It will be recognized that other cell types, vectors, promoters, and other elements used for expression may be readily substituted according to well known principals. At minimum, a vector construct containing the leaderless protein must have a promoter sequence that is active in the target cell. Optionally, and preferably, the construct contains an enhancer, a transcription terminator, and a selectable marker. Such vectors are chosen to be suitable for the species or tissue type of the transfected cell. The cell may be mammalian, avian, or other eukaryotic cell, including yeast, in origin.

Mammalian cells suitable for carrying out the present invention include, amongst others, COS (ATCC No. CRL 1650), BHK (ATCC No. CRL 6281), CHO (ATCC No. CCL 61), HeLa (ATCC No. CCL2), 293 (ATCC No. 1573), NS-1 (ATCC No. T1B18), and Hep G2 (ATCC No. HB 8065).

A wide variety of promoters may be used within the context of the present invention. The choice of promoter will depend, at least in part, on the recipient cell line for transfection. By way of examples, promoters such as the SV40 promoter described above, MoMuLV LTR, RSV LTR, adenoviral promoter, metallothionein gene promoter, cytomegalovirus immediate early promoter or late promoter may be used. A tissue specific promoter may also be used, as long as it is activated in the target cell. For example, the immunoglobulin promoter can be used to express genes in B lymphocytes. Preferred promoters express the leaderless protein at high levels.

Assays to detect leaderless protein, secreted protein, and cytosolic protein include immunoprecipitation of proteins labeled in a pulse-chase procedure, ELISA, Western Blot, biological assays, and phagokinetic tracts. In all these assays, test cells expressing and exporting a leaderless protein are incubated with and without the candidate inhibitor.

Immunoprecipitation is a preferred assay to determine inhibition. Briefly, for immunoprecipitation, cells expressing a leaderless protein from an introduced vector construct, are labeled with $^{35}$S-methionine or $^{35}$S-cysteine for a brief period of time, typically 15 minutes, in methionine- and cysteine-free cell culture medium. Following pulse-labeling, cells are washed with medium supplemented with excess unlabeled methionine and cysteine plus heparin if the leaderless protein is heparin-binding. Cells are then cultured in the same chase medium for various periods of time. Candidate inhibitors are added to cultures at various concentration. Culture supernatant is collected and clarified. Supernatants are incubated with anti-FGF-2 immune serum or a monoclonal antibody, followed by a developing reagent such as *Staphylococcus aureus* Cowan strain I, protein A-Sepharose®, or Gamma-bind™ G-Sepharose®. Immune complexes are pelleted by centrifugation, washed in a buffer containing 1% NP-40 and 0.5% deoxycholate, EGTA, PMSF, aprotinin, leupeptin, and pepstatin. Precipitates are then washed in a buffer containing sodium phosphate, pH 7.2, deoxycholate, NP-40, and SDS. Immune complexes are eluted into an SDS gel sample buffer and separated by SDS-PAGE. The gel is processed for fluorography, dried and exposed to x-ray film.

Alternatively, an ELISA is used to detect and quantify the amount of FGF-2 or other leaderless protein in cell supernatants. Briefly, when FGF-2 is the test leaderless protein, 96-well plates are coated with an anti-FGF-2 antibody, washed, and supernatant is added to the wells. Following incubation and washing, a second antibody to FGF-2 is added. Following further incubation, a developing reagent is added and the amount of FGF-2 determined using an ELISA plate reader. The developing reagent is typically an anti-isotype antibody coupled with an enzyme, such as horseradish peroxidase, which acts upon a substrate resulting in a colorimetric reaction. It will be recognized that rather than using a second antibody coupled to an enzyme, the anti-FGF-2 antibody may be directly coupled to the horseradish peroxidase, or other equivalent detection reagent. If necessary, cell supernatants may be concentrated to raise the detection level.

Alternatively, concentrated supernatant may be electrophoresed on an SDS-PAGE gel and transferred to a solid support, such as nylon or nitrocellulose. The leaderless protein is then detected by an immunoblot (Harlow, *Antibodies. A Laboratory Manual*, Cold Spring Harbor Laboratory, 1988), using an antibody to the leaderless protein containing an isotopic or non-isotopic reporter group. These reporter groups include, but are not limited to enzymes, cofactors, dyes, radioisotopes, luminescent molecules, fluorescent molecules and biotin. Preferably, the reporter group is $^{125}$I or horseradish peroxidase, which may be detected by incubation with 2,2'-azino-di-3-ethylbenzthiazoline sulfonic acid.

An alternative assay, a bioassay, may be performed to quantify the amount of the leaderless protein exported into a cell medium. For example, the bioactivity of the 18 kD FGF-2 may be measured by a proliferation assay, such as the incorporation of tritiated thymidine. Briefly, cells transfected with an expression vector containing FGF-2 are cultured for approximately 30 hours, during which time a candidate inhibitor is added. Following incubation, cells are transferred to a low serum medium for a further 16 hours of incubation. The medium is removed and clarified by centrifugation. A lysis buffer containing protease inhibitors is added. FGF-2 is enriched by binding to heparin-Sepharose® CL-6B and eluted with 3.0M NaCl, after non-FGF-2 proteins are eluted with 1.0M NaCl. Bioactivity of the FGF-2 is then measured by adding various amounts of the eluate to cultured quiescent 3T3 cells. Tritiated thymidine is added to the medium and TCA precipitable counts are measured approximately 24 hours later. For a standard, purified recombinant human FGF-2 may be used.

For leaderless proteins, that cause cell motility, such as FGF-2, a phagokinetic tract assay may be used to determine the amount of leaderless protein exported (Mignatti et al., *J. Cellular Physiol.* 151:81–93, 1992). In this assay, cells are allowed to migrate and microscope cover slip coated with colloidal gold. Under dark field illumination, the gold particles appear as a homogenous layer of highly refringent particles on a dark background. When a cell migrates on the substrate, it pushes aside the gold particles producing a dark track. An image analyzer may be used to measure the length of the tracks. Under conditions cell motility directly correlates with the amount of FGF-2 produced by the cells. The choice of the bioassay will depend, at least in part, by the leaderless protein tested.

In any of these assays, a cardiac glycoside or aglycone derivative inhibits export if there is a statistically significant reduction in the amount of protein detected extracellularly in the assay performed with the inhibitor compared to the assay performed without the inhibitor. Preferably, the inhibitor reduces export of the leaderless protein by at least 50%, even more preferably 80% or greater, and also preferably, in a dose-dependent manner. In addition, there should be no statistically significant effect on the appearance of either the secreted protein or the cytosolic protein. Preferably, there is less than a 10% increase or decrease in the appearance of these two proteins.

Administration

As described above, an inhibitor of the export of a leaderless protein is useful for treating tumors, inhibiting proliferation of cells, including smooth muscle cells that cause restenosis, and treating complications of diabetes, among other uses. Treatment means that symptoms may be lessened or the progression of the disease or conditions halted or delayed. Cells to be treated are contacted with a cardiac glycoside or aglycone derivative of a cardiac glycoside at a therapeutically effective dosage. Contacting may be effected by incubation of cells ex vivo or in vivo, such as by topical treatment, delivery by specific carrier or by vascular supply.

The conjugates herein may be formulated into pharmaceutical compositions suitable for topical, local, intravenous and systemic application. Time release formulations are also desirable. Effective concentrations of one or more of the conjugates are mixed with a suitable pharmaceutical carrier or vehicle. The concentrations or amounts of the conjugates that are effective requires delivery of an amount, upon administration, that ameliorates the symptoms or treats the disease. Typically, the compositions are formulated for single dosage administration. Therapeutically effective concentrations and amounts may be determined empirically by testing the conjugates in known in vitro and in vivo systems, such as those described herein; dosages for humans or other animals may then be extrapolated therefrom.

Candidate tumors for treatment as described herein include those with receptors for FGF. Such tumors include melanomas, teratocarcinomas, ovarian carcinomas, bladder tumors, and neuroblastomas.

Other diseases, disorders, and syndromes are suitable for treatment. Diabetic complications, such as diabetic retinopathy, restenosis, polycystic kidney disease, and atherosclerosis are also candidates for such treatments. Cells in the eye, kidney and peripheral nerve, which are affected in diabetes, may be treated with the conjugates described herein.

Pharmaceutical carriers or vehicles suitable for administration of the conjugates provided herein include any such carriers known to those skilled in the art to be suitable for the particular mode of administration. In addition, the inhibitor may be formulated as the sole pharmaceutically active ingredient in the composition or may be combined with other active ingredients.

The compositions of the present invention may be prepared for administration by a variety of different routes. Local administration of the cardiac glycosides or aglycone derivatives is preferred. The inhibitor may be mixed with suitable excipients, such as salts, buffers, stabilizers, and the like. If applied topically, such as to the skin and mucous membranes, the inhibitor may be in the form of gels, creams, and lotions. Such solutions, particularly those intended for ophthalmic use, may be formulated as 0.01%–10% isotonic solutions, pH about 5–7, with appropriate salts (see, e.g., U.S. Pat. No. 5,116,868).

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The inhibitor may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponge (see, e.g., U.S. Pat. Nos. 3,956,044 and 4,045,238).

The inhibitors can be administered by any appropriate route, for example, orally, parenterally, intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors and restenosis will typically be treated by systemic, intradermal or intramuscular modes of administration.

The inhibitor is included in the pharmaceutically acceptable carrier in an amount sufficient to exert a therapeutically useful effect in the absence of undesirable side effects. It is understood that number and degree of side effects depends upon the condition for which the conjugates are administered. For example, certain toxic and undesirable side effects are tolerated when treating life-threatening illnesses, such as tumors, that would not be tolerated when treating disorders of lesser consequence. The concentration of conjugate in the composition will depend on absorption, inactivation and excretion rates thereof, the dosage schedule, and amount administered as well as other factors known to those of skill in the art.

The inhibitor may be administered one time, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The following examples are offered by way of illustration and not by way of limitation.

EXAMPLE 1

CONSTRUCTION OF PLASMID EXPRESSING FGF-2

The expression vector containing the 18 kD isoform of FGF-2 was constructed as follows. The sequence of the 18 kD isoform of human FGF-2 was provided by plasmid 18dx (Florkiewicz and Sommer, *Proc. Natl. Acad. Sci. USA* 86:3978–3981, 1989). This vector only expresses the 18 kD isoform because the sequences upstream of the ApaI site located 11 bp 5' of the ATG codon initiating translation of the 18 kD FGF-2 isoform were deleted. Briefly, plasmid p18dx was linearized with ApaI and an oligonucleotide adaptor containing an XhoI site was ligated to the plasmid. The XhoI restriction fragment containing FGF-2 was purified and subloned into the XhoI site of pJC119 (Sprague et al., supra).

An expression vector encoding hCG-alpha was provided by Dr. Carolyn Machamer (Dept. of Cell Biology, Johns Hopkins Medical School) and is identical to Guan et al. (J. Biol. chem. 263:5306–5313, 1988).

EXAMPLE 2

CELL CULTURE, TRANSFECTION, AND METABOLIC LABELING

COS-1 cells obtained from the American Type Culture Collection (ATCC CRL 1650) are cultured in DMEM supplemented with 10% fetal bovine serum, 2 mM L-glutamine, 1 mM sodium pyruvate, 100 U/mL penicillin, and 100 U/mL streptomycin. COS-1 cells are transfected with 10 μg of CsCl-purified plasmid DNA in 1 ml of transfection buffer (140 mM NaCl, 3 mM KCl, 1 mM $CaCl_2$, 0.5 mM $MgCl_2$, 0.9 mM $Na_2HPO_4$, 25 mM Tris, pH 7.4. The plasmid 18dx was co-transfected with pMAMneo (Clontech, Palo Alto, Calif.), which contains the selectable marker neomycin phosphotransferase. When 2 μg of p18dx was co-transfected with 10 μg of pMAMneo, greater than 70% of transfected cells expressed both FGF-2 and neo, as determined by immunofluorescence microscopy.

At 40 to 48 hours post-DNA transfection, COS-1 cells were metabolically pulse-labeled for 15 min with 100 μCi of $^{35}S$-methionine and $^{35}S$-cysteine (Trans $^{35}S$-label, ICN Biomedicals, Irvine, Calif.) in 1 ml of met and cysteine free DMEM. Following labeling, the cell monolayers were washed once with DMEM supplemented with excess (10 mM) unlabeled methionine and cysteine plus 25 μg/ml heparin. Cells were then cultured in 2 ml of this medium for the indicated lengths of time. For the indicated cultures, chase medium was supplemented with ouabain at the indicated concentrations.

EXAMPLE 3

IMMUNOPRECIPITATION AND WESTERN BLOT ANALYSIS

Cell and conditioned medium fractions are prepared for immunoprecipitation essentially as described previously (Florkiewicz et al., Growth Factors 4:265–275, 1991; Florkiewicz et al., Ann. N.Y. Acad Sci. 638:109–126) except that 400 μl of lysis buffer (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) was added to the medium fraction after clarification by centrifugation in a microfuge for 15 min. Cell or medium fractions are incubated with guinea pig anti-FGF-2 immune serum (1:200) at 21° C. for 40 min. GammaBind™ G Sepharose® (Pharmacia LKB Biotechnology, Uppsala, Sweden) was added for an additional 30 min incubation. Immune complexes were pelleted by microphuge centrifugation, washed three times with lysis buffer and four times with ice cold Immunoprecipitation wash buffer (0.15M NaCl, 0,01M Na-phosphate pH 7.2, 1% deoxycholate, 1% NP-40, 0.1% sodium dodecyl sulfate). Immune complexes were eluted into SDS gel sample buffer 125 mM Tres, pH 6.8, 4% SDS, 10% glycerol, 0.004% bromphenol blue, 2 mM EGTA and separated by 12% SDS-PAGE. The gel was processed for fluorography, dried, and exposed to X-ray film at −70° C. When neomycin phosphotransferase was immunoprecipitated, a rabbit anti-NPT antibody (5Prime-3Prime, Boulder, Colo.) was used.

For Western blot analysis, proteins were transferred from the 12% SDS-PAGE gel to a nitrocellulose membrane (pore size 0.45 μm in cold buffer containing 25 mM 3-[dimethyl (hydroxymethyl)methylamino]-2-hydroxypropane-sulfonic acid, pH 9.5, 20% methanol for 90 min at 0.4 amps. Membranes were blocked in 10 mM Tris, pH7.5, 150 mM NaCl, 5 mM $NaN_3$, 0.35% polyoxyethylene-sorbitan monolaurate, and 5% nonfat dry milk (Carnation Co., Los Angeles, Calif.) for 1 hr at room temperature. Membranes were incubated with a monoclonal anti-FGF-2 antibody (Transduction Laboratories, Lexington, Ky.) at 0.3 μg/ml in blocking buffer at 4° C. for 16 hr. Following incubation, membranes were washed at room temperature with 10 changes of buffer containing 150 mM NaCl, 500 mM sodium phosphate pH 7.4, 5 mM $NaN_3$, and 0.05% polyoxyethylene-sorbitan monolaurate. Membranes were then incubated in blocking buffer containing 1 μg/ml rabbit anti-mouse IgG (H+L), affinipure, Jackson Immuno Research Laboratories, West Grove, Pa.) for 30 min at room temperature. Membranes were subsequently washed in 1 l of buffer described above, and incubated for 1 hr in 100 ml of blocking buffer containing 15 μCi $^{125}I$-protein A (ICN Biochemicals, Costa Mesa, Calif.), and washed with 1 l of buffer. The radiosignal was visualized by autoradiography.

EXAMPLE 4

FGF-2 BIOASSAY

The bioactivity of FGF-2 may be measured in a thymidine incorporation assay. Cells transfected with FGF-2 as described above are incubated for 30 hr. At this time, the culture medium is replaced with 6 ml of DMEM containing 0.5% FBS (low serum medium) for 16 hr. The medium is removed, clarified by centrifugation in a microfuge for 15 min at 4° C. An equal volume of lysis buffer and heparin-Sepharose® CL-6B is added and the mixture incubated with rocking for 2 hr at 4° C. The Sepharose is pelleted and washed three times with lysis buffer followed by three washes with HS-wash buffer (20 mM Tris, pH 7.4, 5 mM EDTA, 2 mM EGTA, plus protease inhibitors, 0.5M NaCl) and washed three times with HS-wash buffer containing 1M NaCl. Proteins that remained bound to the Sepharose were eluted into HS wash buffer containing 3M NaCl.

The stimulation of DNA synthesis was measured in quiescent Swiss 3T3 cells (clone NR-6) as previously described (Witte et al., J. Cell Physiol. 137:86–94, 1988; Florkiewicz and Sommer Proc. Natl. Acad. Sci. USA 86:3978–3981, 1989). Briefly, cells were plated at low density and growth arrested by culturing for 72 hr in 1 ml of media containing 0.1% FBS. Various amounts of the 3M NaCl HS-eluate are added directly to the culture medium and the level of [$^3H$]-thymidine incorporation into TCA precipitable counts was measured 20–24 hr later. As a control, 1 pg to 1 ng of recombinant human FGF-2 was added to the cells in a similar manner.

EXAMPLE 5

BREFELDIN-RESISTANT EXPORT OF FGF-2

Brefeldin A inhibits secretion of proteins from the ER and Golgi. In contrast, export of a leaderless protein is not inhibited by treatment with Brefeldin A.

COS-1 cells are obtained from the American Type Culture Collection and cultured in Dulbecco's Modified Eagle Medium (DMEM, University of California San Diego Core Facility) supplemented with 10% fetal bovine serum (Gemini Bioproducts, Inc.), 2 mM L-glutamine, 1 mM sodium pyruvate, 0.1 mM non-essential amino acids, 100 units/ml penicillin, and 100 units/ml streptomycin. The plasmid SV-40-based expression vector containing the wild type (human) CDNA encoding multiple FGF-2 isoforms (24, 23, 22 and 18-kD) has been described previously (Florkiewicz and Sommer, supra). Approximately 3×10$^5$ COS-1 cells in a 60 mm tissue culture dish are transfected with 10 μg of CsCl-purified plasmid DNA mixed with 1.0 ml of transfection buffer (140 mM NaCl, 3 mM KCl, 1 mM $CaCl_2$, 0.5 mM $MgCl_2$, 0.9 mM $Na_2HPO_4$, 25 mM Tris pH 7.4; all from Sigma Chemical Company). Under these co-transfection conditions using 2 μg of p18dx plus 10 μg pMAMneo, greater than 70% of transfected cells express both proteins, as determined by immunofluorescence microscopy. The ratio of plasmid DNA may be varied with insignificant change in results. Forty to 48 hours post-DNA transfection COS-1 cells are metabolically pulse-labeled for 15 minutes with 100 μCi of $^{35}$S-methionine and $^{35}$S-cysteine (Trans$^{35}$S-label, ICN Biomedicals, Inc.) in 1.0 ml of methionine- and cysteine-free DMEM. After pulse-labeling, the cell monolayers are washed once with DMEM supplemented with excess (10 mM) unlabeled methionine (Sigma Chemical Company) and cysteine (Sigma Chemical Company) and then cultured in 1.0 ml of the same medium (chase) for the indicated lengths of time. Cultures treated with Brefeldin A include 15 μg/ml of Brefeldin A in the chase medium. Chase medium is also supplemented with 25 μg/ml heparin (Sigma Chemical Company). Although heparin is not necessary to qualitatively detect FGF-2 export, it is necessary in order to quantitatively detect the export of FGF-2 in this assay.

Cell and medium fractions are prepared for immunoprecipitation essentially as described previously (Florkiewicz et al., 1991) except that 400 μl of lysis buffer without NaCl (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, and 10 ng/ml pepstatin) is added to the medium fraction clarified by microfuge centrifugation for 15 minutes at 4° C. before adding immune serum. Both cell and medium fractions are incubated with a 1:200 dilution of guinea pig anti-FGF-2 immune serum (prepared in our laboratory) at 21° C. for 40 minutes and then GammaBind G Sepharose® (Pharmacia LKB Biotechnology) is added for an additional 30 minutes incubation. G-Sepharose-bound immune complexes are pelleted, washed three times with lysis buffer and four times with ice cold immunoprecipitation wash buffer (0.15M NaCl, 0.01M Na-Phosphate pH 7.2, 1% deoxycholate, 1% NP-40, 0.1% sodium dodecyl sulfate). Immune complexes are eluted directly into SDS-gel-sample buffer and separated by 12% SDS-polyacrylamide gel electrophoresis (PAGE). The gel is processed for fluorography, dried and exposed to X-ray film at −70° C. For immunoprecipitations involving ncomycin phosphotransferase (NPT), rabbit anti-NPT antibody (5 Prime- 3 Prime, Inc., Boulder, Colo.) was used.

Figures 5A, 5B, 5C:
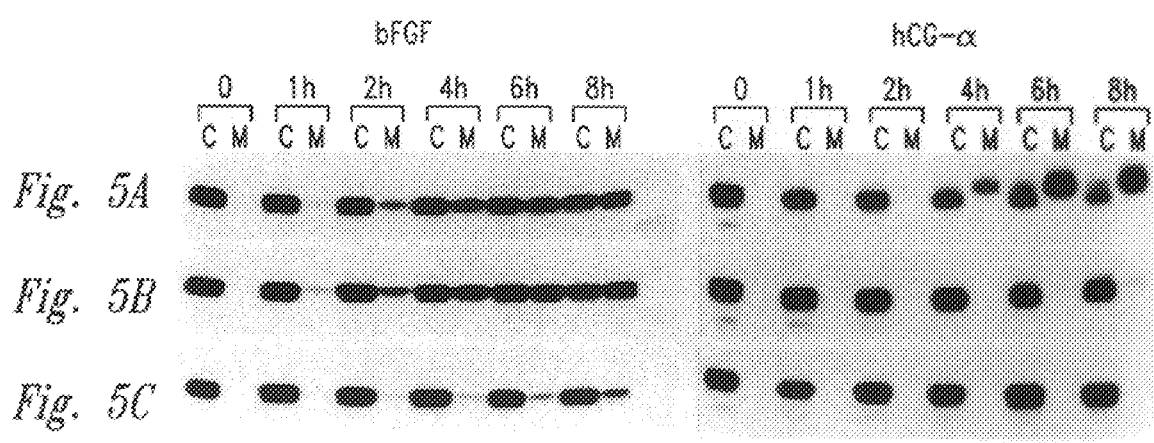
FIG. 5 is a photograph of immunoprecipitated FGF-2 and HCG-α from cellular (C) and medium (M) fractions following metabolic labeling. COS-1 cells were transfected with p18dx or hCG-α and metabolically labeled in medium alone (A), Brefedin A (B) or 2-deoxy-D-glucose plus $NaN_3$ (C). FGF-2 and HCG-α were immunoprecipitated from cells (C) or medium (M), electrophoresed and autoradiographed.

As shown in FIG. 5, the export of 18 kD FGF-2 is brefeldin A-resistant and is energy dependent. Sample A was chased with medium alone, sample B was chased with medium supplemented with 25 μg/ml Brefeldin A and sample C was chased with medium supplemented with 50 mM 2-deoxy-D-glucose and NaN$_3$. As shown in FIG. 5, FGF-2 is exported to the medium by 2 hours. Brefeldin A had no substantial effect on this export. However, when NaN$_3$, a metabolic inhibitor, is present, export is substantially reduced. In contrast, hCG-α is secreted into the medium by 4 hours and is brefeldin sensitive and energy dependent. hCG-α contains a hydrophobic leader (signal) sequence and as a consequence is secreted via the ER and Golgi.

EXAMPLE 6

INHIBITION OF LEADERLESS PROTEINS

COS cells are co-transfected as described above with plasmids expressing FGF2, hCG-α or neomycin. Metabolic labeling is performed as described above, except that during the chase period, inhibitor is added at 10 nM to 1 mM in log increments. At the end of the chase, cells and cell media are harvested and processed for immune precipitations as described above.

Figure 2A:
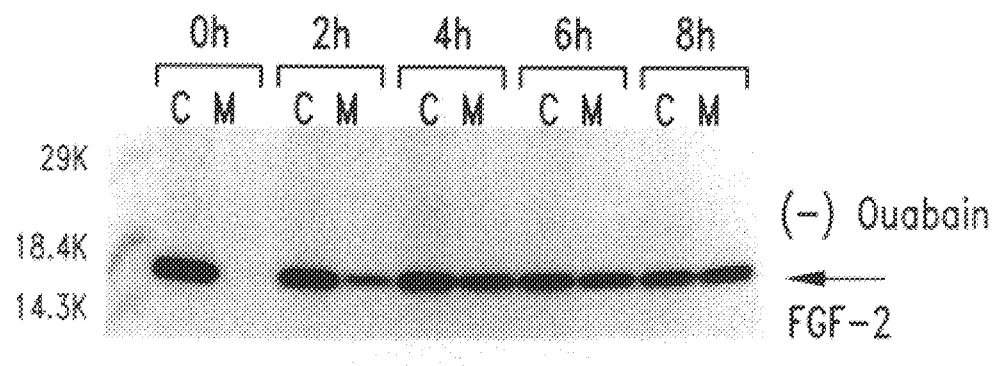
FIG. 2 is an SDS-PAGE gel of pulse-labeled, immunoprecipitated cellular (lanes marked C) and extracellular FGF-2 (lanes marked M) following treatment without ouabain (panel A) and with ouabain (panel B).
Figure 2B:
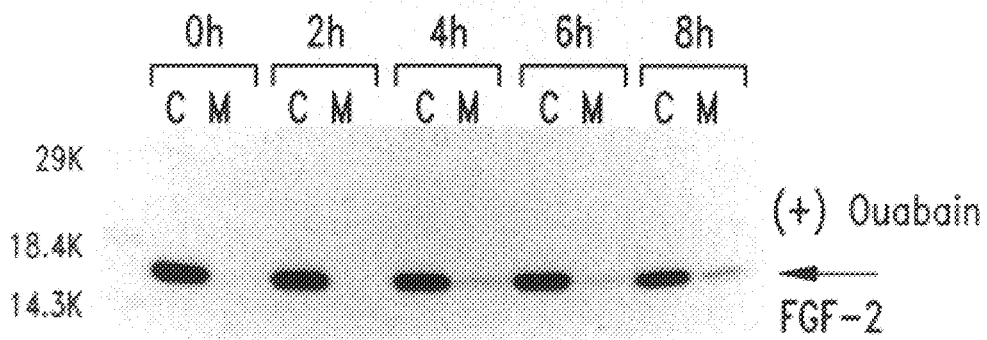
Figure 3A:
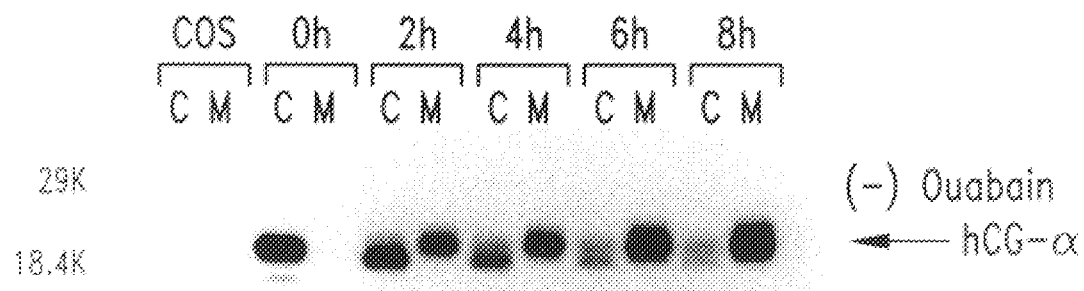
FIG. 3 is an SDS-PAGE gel of pulse-labeled, immunoprecipitated cellular (lanes marked C) and extracellular (lanes marked M) human corionic gonadatrophin a following treatment without ouabain (panel A) and with ouabain (panel B).
Figure 3B:
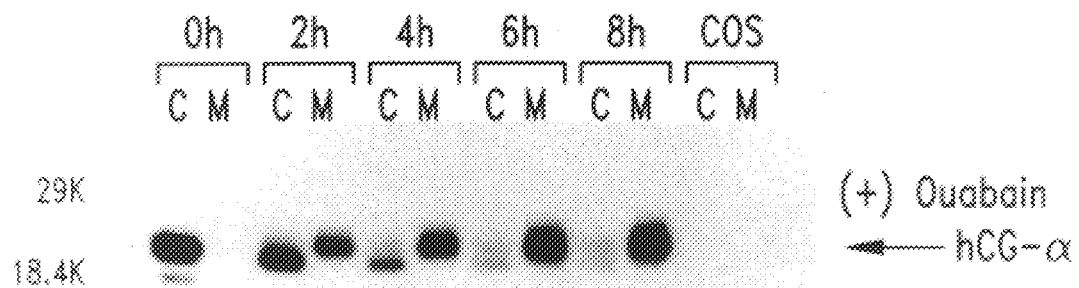
Figure 4:
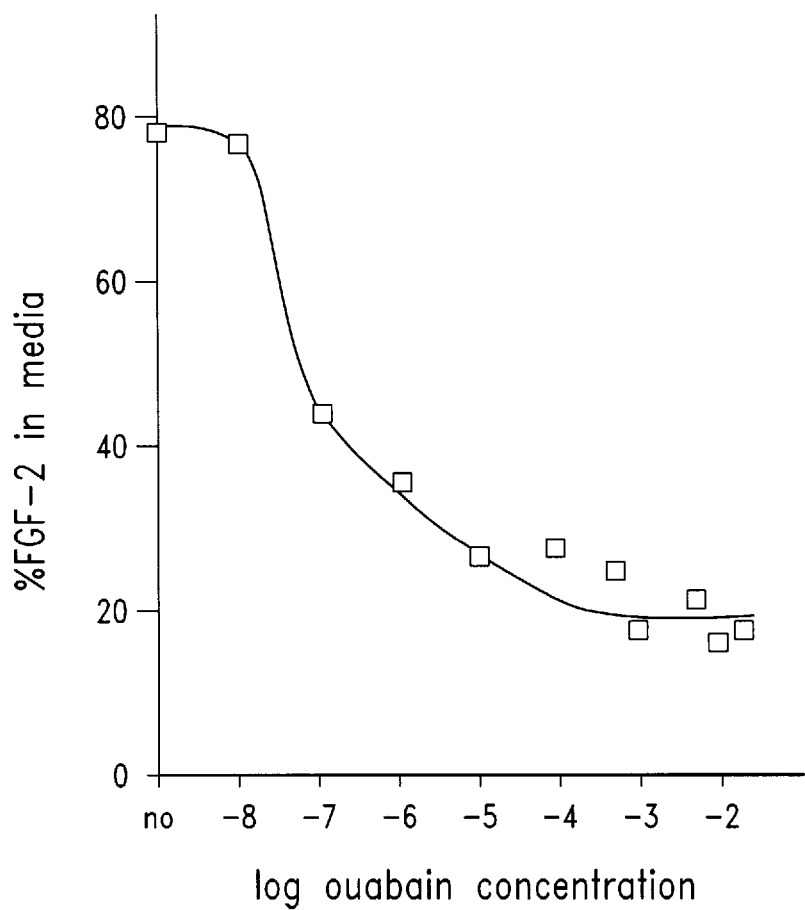
FIG. 4 is a graph showing the quantitation of FGF-2 export following treatment with ouabain.

Ouabain and digoxin inhibited the export of FGF-2, but not human chorionic gonadatrophin α. Ouabain inhibited 50% of export at approximately 0.1 μM and digoin at approximately 5 μM. Further experiments with ouabain demonstrate that inhibition is time-dependent (FIG. 2), does not affect secretion of hCG-α (FIG. 3) and inhibits export of FGF-2 in a dose-dependent manner (FIG. 4).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method of inhibiting the export of a translated leaderless protein from a cell expressing the protein, comprising contacting the cell with a cardiac glycoside, therefrom inhibiting the export of the leaderless protein.

2. The method of claim 1 wherein the cardiac glycoside is selected from the group consisting of digoxin, strophanthin K, digitoxin, lanatoside A, ouabain, digitoxose, gitoxin, oleandrin and acovenoside A.

3. The method of claim 1 wherein the cardiac glycoside is ouabain.

4. The method of claim 1 wherein the cardiac glycoside is digoxin.

5. The method of claim 1 wherein the leaderless protein is selected from the group consisting of FGF-1, FGF-2, IL-1α, IL-1β, PD-ECGF, CNTF, thymosin, parathymosin and factor XIIIa, vas deferens protein, sciatic nerve growth-promoting activity, transglutaminase, L-14 lectin, thioredoxin-like protein and int-2.

6. The method of claim 1 wherein the leaderless protein is FGF-2.

7. A method of inhibiting the export of a translated leaderless protein from a cell expressing the protein, comprising contacting the cell with an aglycone derivative of a cardiac glycoside, therefrom inhibiting the export of the leaderless protein.

8. The method of claim 7 wherein the aglycone derivative is selected from the group consisting of strophanthidin, digoxigenin, digitoxigenin and uzarigenin.

9. The method of claim 7 wherein the aglycone derivative is digoxigenin.

10. A method of inhibiting the export of translated FGF-2 protein from a cell expressing FGF-2, comprising contacting the cell with a cardiac glycoside, therefrom inhibiting the export of FGF-2.

11. The method of claim 10 wherein the cardiac glycoside is selected from the group consisting of digoxin, strophanthin K, digitoxin, lanatoside A, ouabain, digitoxose, gitoxin, oleandrin and acovenoside A.

12. The method of claim 10 wherein the cardiac glycoside is ouabain.

13. The method of claim 10 wherein the cardiac glycoside is digoxin.

14. A method of inhibiting the export of translated FGF-2 protein from a cell expressil, the protein, comprising contacting the cell with an aglycone derivative of a cardiac glycoside, therefrom inhibiting the export of FGF-2.

15. The method of claim 14 wherein the aglycone derivative is selected from the group consisting of digoxigenin, digitoxigenin and uzarigenin.

16. The method of claim 14 wherein the aglycone derivative is digoxigenin.

17. A method of inhibiting the export of a translated leaderless protein from a cell expressing the protein, comprising treating cells with a compound selected from the group consisting of:

formula I:

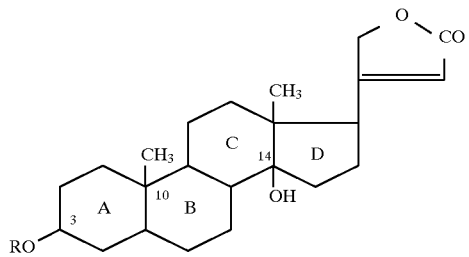

wherein R=digitoxose$_3$-D-glucose, acetylated digitoxose$_3$-D-glucose, digitoxose$_3$, or acetylated digitoxose$_3$;

formula II:

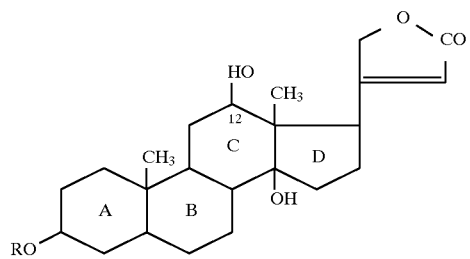

wherein R=digitoxose$_3$-D-glucose or acetylated digitoxose$_3$-D-glucose, formula III:

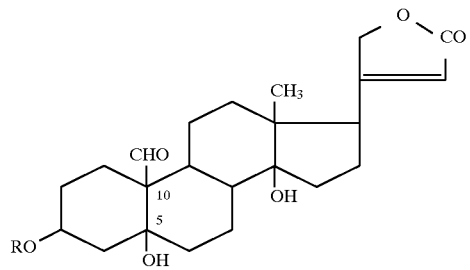

wherein R=cymarose-$\beta$-D glucose-$\alpha$-D glucose or cymarose-$\beta$-D-glucose;

formula IV:

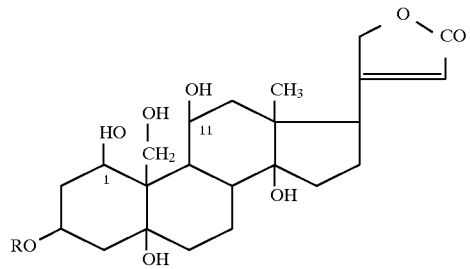

wherein R=L-rhamnose; and formula V:

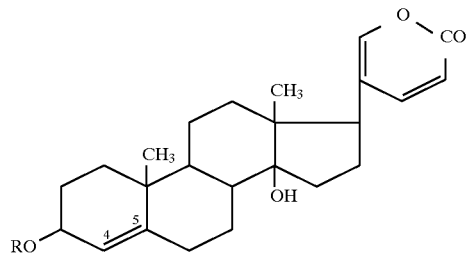

wherein R=L-rhamnose or L-rhamnose-D-glucose.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 3877 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GCCAGATTAG    CGGACGCGTG    CCCGCGGTTG    CAACGGGATC    CCGGGCGCTG    CAGCTTGGGA         60

GGCGGCTCTC    CCCAGGCGGC    GTCCGCGGAG    ACAACCATCC    GTGAACCCCA    GGTCCCGGCG        120

CGCCGGCTCG    CCGCGCACCA    GGGGCCGGCG    GACAGAAGAG    CGGCCGAGCG    GCTCGAGGCT        180

GGGGGACCCG    GCGCGGCCGC    GCGCTGCCGG    GCGGGAGGCT    GGGGGGCCGG    GGCGGGGCCG        240

TGCCCCGGAG    CGGGTCGGAG    GCCGGGGCCG    GGGCCGGGGG    ACGGCGGCTC    CCCGCGCGGC        300

TCCAGCGGCT    CGGGGATCCC    GGCCGGGCCC    CGCAGGACCA    TGGCAGCCGG    GAGCATCACC        360
```

```
ACGCTGCCCG CCTTGCCCGA GGATGGCGGC AGCGGCGCCT TCCCGCCCGG CCACTTCAAG    420
GACCCCAAGC GGCTGTACTG CAAAAACGGG GGCTTCTTCC TGCGCATCCA CCCCGACGGC    480
CGAGTTGACG GGGTCCGGGA GAAGAGCGAC CCTCACATCA AGCTACAACT TCAAGCAGAA    540
GAGAGAGGAG TTGTGTCTAT CAAAGGAGTG TGTGCTAACC GTTACCTGGC TATGAAGGAA    600
GATGGAAGAT TACTGGCTTC TAAATGTGTT ACGGATGAGT GTTTCTTTTT TGAACGATTG    660
GAATCTAATA ACTACAATAC TTACCGGTCA AGGAAATACA CCAGTTGGTA TGTGGCACTG    720
AAACGAACTG GGCAGTATAA ACTTGGATCC AAAACAGGAC CTGGGCAGAA AGCTATACTT    780
TTTCTTCCAA TGTCTGCTAA GAGCTGATTT TAATGGCCAC ATCTAATCTC ATTTCACATG    840
AAAGAAGAAG TATATTTTAG AAATTTGTTA ATGAGAGTAA AAGAAATAA ATGTGTAAAG      900
CTCAGTTTGG ATAATTGGTC AAACAATTTT TTATCCAGTA GTAAAATATG TAACCATTGT    960
CCCAGTAAAG AAAAATAACA AAGTTGTAA AATGTATATT CTCCCTTTTA TATTGCATCT    1020
GCTGTTACCC AGTGAAGCTT ACCTAGAGCA ATGATCTTTT TCACGCATTT GCTTTATTCG   1080
AAAAGAGGCT TTTAAAATGT GCATGTTTAG AAACAAAATT TCTTCATGGA AATCATCATA   1140
TACATTAGAA AATCACAGTC AGATGTTTAA TCAATCCAAA ATGTCCACTA TTTCTTATGT   1200
CATTCGTTAG TCTACATGTT TCTAAACATA TAAATGTGAA TTTAATCAAT TCCTTTCATA   1260
GTTTTATAAT TCTCTGGCAG TTCCTTATGA TAGAGTTTAT AAAACAGTCC TGTGTAAACT   1320
GCTGGAAGTT CTTCCACAGT CAGGTCAATT TTGTCAAACC CTTCTCTGTA CCCATACAGC   1380
AGCAGCCTAG CAACTCTGCT GGTGATGGGA GTTGTATTTT CAGTCTTCGC CAGGTCATTG   1440
AGATCCATCC ACTCACATCT TAAGCATTCT TCCTGGCAAA AATTTATGGT GAATGAATAT   1500
GGCTTTAGGC GGCAGATGAT ATACATATCT GACTTCCCAA AAGCTCCAGG ATTTGTGTGC   1560
TGTTGCCGAA TACTCAGGAC GGACCTGAAT TCTGATTTTA TACCAGTCTC TTCAAAACCT   1620
TCTCGAACCG CTGTGTCTCC TACGTAAAAA AAGAGATGTA CAAATCAATA ATAATTACAC   1680
TTTTAGAAAC TGTATCATCA AAGATTTTCA GTTAAAGTAG CATTATGTAA AGGCTCAAAA   1740
CATTACCCTA ACAAAGTAAA GTTTTCAATA CAAATTCTTT GCCTTGTGGA TATCAAGAAA   1800
TCCCAAAATA TTTTCTTACC ACTGTAAATT CAAGAAGCTT TTGAAATGCT GAATATTTCT   1860
TTGGCTGCTA CTTGGAGGCT TATCTACCTG TACATTTTG GGGTCAGCTC TTTTTAACTT    1920
CTTGCTGCTG TTTTTCCCAA AAGGTAAAAA TATAGATTGA AAAGTTAAAA CATTTTGCAT   1980
GGCTGCAGTT CCTTTGTTTC TTGAGATAAG ATTCCAAAGA ACTTAGATTT ATTTCTTCAA   2040
CACCGAAATG CTGGAGGTGT TTGATCAGTT TTCAAGAAAC TTGGAATATA AATAATTTTA   2100
TAATTCAACA AAGGTTTTCA CATTTATAA GGTTGATTTT TCAATTAAAT GCAAATTTAT    2160
GTGGCAGGAT TTTTATTGCC ATTAACATAT TTTTGTGGCT GCTTTTCTA CACATCCAGA    2220
TGGTCCCTCT AACTGGGCTT TCTCTAATTT TGTGATGTTC TGTCATTGTC TCCCAAAGTA   2280
TTTAGGAGAA GCCCTTTAAA AAGCTGCCTT CCTCTACCAC TTTGCTGAAA GCTTCACAAT   2340
TGTCACAGAC AAAGATTTTT GTTCCAATAC TCGTTTTGCC TCTATTTTAC TTGTTTGTCA   2400
AATAGTAAAT GATATTTGCC CTTGCAGTAA TTCTACTGGT GAAAAACATG CAAAGAAGAG   2460
GAAGTCACAG AAACATGTCT CAATTCCCAT GTGCTGTGAC TGTAGACTGT CTTACCATAG   2520
ACTGTCTTAC CCATCCCCTG GATATGCTCT TGTTTTTTCC CTCTAATAGC TATGGAAAGA   2580
TGCATAGAAA GAGTATAATG TTTTAAAACA TAAGGCATTC GTCTGCCATT TTTCAATTAC   2640
ATGCTGACTT CCCTTACAAT TGAGATTTGC CCATAGGTTA AACATGGTTA GAAACAACTG   2700
AAAGCATAAA AGAAAAATCT AGGCCGGGTG CAGTGGCTCA TGCCCATATT CCCTGCACTT   2760
```

-continued

```
TGGGAGGCCA AAGCAGGAGG ATCGCTTGAG CCCAGGAGTT CAAGACCAAC CTGGTGAAAC    2820

CCCGTCTCTA CAAAAAAACA CAAAAAATAG CCAGGCATGG TGGCGTGTAC ATGTGGTCTC    2880

AGATACTTGG GAGGCTGAGG TGGGAGGGTT GATCACTTGA GGCTGAGAGG TCAAGGTTAC    2940

AGTGAGCCAT AATCGTGCCA CTGCAGTCCA GCCTAGGCAA CAGAGTGAGA CTTTGTCTCA    3000

AAAAAGAGA AATTTTCCTT AATAAGAAAA GTAATTTTTA CTCTGATGTG CAATACATTT     3060

GTTATTAAAT TTATTATTTA AGATGGTAGC ACTAGTCTTA AATTGTATAA AATATCCCCT    3120

AACATGTTTA AATGTCCATT TTTATTCATT ATGCTTTGAA AATAATTAT GGGGAAATAC     3180

ATGTTTGTTA TTAAATTTAT TATTAAAGAT AGTAGCACTA GTCTTAAATT TGATATAACA    3240

TCTCCTAACT TGTTAAATG TCCATTTTA TTCTTTATGT TTGAAAATAA ATTATGGGA       3300

TCCTATTTAG CTCTTAGTAC CACTAATCAA AAGTTCGGCA TGTAGCTCAT GATCTATGCT    3360

GTTTCTATGT CGTGGAAGCA CCGGATGGGG GTAGTGAGCA AATCTGCCCT GCTCAGCAGT    3420

CACCATAGCA GCTGACTGAA AATCAGCACT GCCTGAGTAG TTTTGATCAG TTTAACTTGA    3480

ATCACTAACT GACTGAAAAT TGAATGGGCA AATAAGTGCT TTTGTCTCCA GAGTATGCGG    3540

GAGACCCTTC CACCTCAAGA TGGATATTTC TTCCCCAAGG ATTTCAAGAT GAATTGAAAT    3600

TTTTAATCAA GATAGTGTGC TTTATTCTGT TGTATTTTTT ATTATTTTAA TATACTGTAA    3660

GCCAAACTGA AATAACATTT GCTGTTTTAT AGGTTTGAAG ACATAGGAAA AACTAAGAGG    3720

TTTTATTTTT GTTTTGCTG ATGAAGAGAT ATGTTAAAT ACTGTTGTAT TGTTTTGTTT      3780

AGTTACAGGA CAATAATGAA ATGGAGTTTA TATTTGTTAT TTCTATTTTG TTATATTTAA    3840

TAATAGAATT AGATTGAAAT AAAATATAAT GGGAAAT                             3877
```

(2) INFORMATION FOR SEQ ID NO:2:

(i) SEQUENCE CHARACTERISTICS:
     (A) LENGTH: 477 base pairs
     (B) TYPE: nucleic acid
     (C) STRANDEDNESS: single
     (D) TOPOLOGY: linear (ix) FEATURE:
     (A) NAME/KEY: CDS
     (B) LOCATION: 1..474

(xi) SEQUENCE DESCRIPTION: SEQ ID NO:2:

```
CGC AGG ACC ATG GCA GCC GGG AGC ATC ACC ACG CTG CCC GCC TTG CCC       48
Arg Arg Thr Met Ala Ala Gly Ser Ile Thr Thr Leu Pro Ala Leu Pro
 1               5                  10                  15

GAG GAT GGC GGC AGC GGC GCC TTC CCG CCC GGC CAC TTC AAG GAC CCC       96
Glu Asp Gly Gly Ser Gly Ala Phe Pro Pro Gly His Phe Lys Asp Pro
             20                  25                  30

AAG CGG CTG TAC TGC AAA AAC GGG GGC TTC TTC CTG CGC ATC CAC CCC      144
Lys Arg Leu Tyr Cys Lys Asn Gly Gly Phe Phe Leu Arg Ile His Pro
         35                  40                  45

GAC GGC CGA GTT GAC GGG GTC CGG GAG AAG AGC GAC CCT CAC ATC AAG      192
Asp Gly Arg Val Asp Gly Val Arg Glu Lys Ser Asp Pro His Ile Lys
     50                  55                  60

CTA CAA CTT CAA GCA GAA GAG AGA GGA GTT GTG TCT ATC AAA GGA GTG      240
Leu Gln Leu Gln Ala Glu Glu Arg Gly Val Val Ser Ile Lys Gly Val
 65                  70                  75                  80

TGT GCT AAC CGT TAC CTG GCT ATG AAG GAA GAT GGA AGA TTA CTG GCT      288
Cys Ala Asn Arg Tyr Leu Ala Met Lys Glu Asp Gly Arg Leu Leu Ala
                 85                  90                  95

TCT AAA TGT GTT ACG GAT GAG TGT TTT TTT TTT GAA CGA TTG GAA TCT      336
Ser Lys Cys Val Thr Asp Glu Cys Phe Phe Phe Glu Arg Leu Glu Ser
```

```
                100                              105                              110
AAT  AAC  TAC  AAT  ACT  TAC  CGG  TCA  AGG  AAA  TAC  ACC  AGT  TGG  TAT  GTG       384
Asn  Asn  Tyr  Asn  Thr  Tyr  Arg  Ser  Arg  Lys  Tyr  Thr  Ser  Trp  Tyr  Val
               115                         120                        125

GCA  CTG  AAA  CGA  ACT  GGG  CAG  TAT  AAA  CTT  GGA  TCC  AAA  ACA  GGA  CCT       432
Ala  Leu  Lys  Arg  Thr  Gly  Gln  Tyr  Lys  Leu  Gly  Ser  Lys  Thr  Gly  Pro
     130                         135                        140

GGG  CAG  AAA  GCT  ATA  CTT  TTT  CTT  CCA  ATG  TCT  GCT  AAG  AGC  TGA            477
Gly  Gln  Lys  Ala  Ile  Leu  Phe  Leu  Pro  Met  Ser  Ala  Lys  Ser
145                      150                        155
```

( 2 ) INFORMATION FOR SEQ ID NO:3:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Arg  Arg  Thr  Met  Ala  Ala  Gly  Ser  Ile  Thr  Thr  Leu  Pro  Ala  Leu  Pro
1                        5                        10                       15

Glu  Asp  Gly  Gly  Ser  Gly  Ala  Phe  Pro  Pro  Gly  His  Phe  Lys  Asp  Pro
               20                       25                       30

Lys  Arg  Leu  Tyr  Cys  Lys  Asn  Gly  Gly  Phe  Phe  Leu  Arg  Ile  His  Pro
               35                       40                       45

Asp  Gly  Arg  Val  Asp  Gly  Val  Arg  Glu  Lys  Ser  Asp  Pro  His  Ile  Lys
     50                       55                       60

Leu  Gln  Leu  Gln  Ala  Glu  Glu  Arg  Gly  Val  Val  Ser  Ile  Lys  Gly  Val
65                       70                       75                       80

Cys  Ala  Asn  Arg  Tyr  Leu  Ala  Met  Lys  Glu  Asp  Gly  Arg  Leu  Leu  Ala
                    85                       90                       95

Ser  Lys  Cys  Val  Thr  Asp  Glu  Cys  Phe  Phe  Phe  Glu  Arg  Leu  Glu  Ser
               100                      105                      110

Asn  Asn  Tyr  Asn  Thr  Tyr  Arg  Ser  Arg  Lys  Tyr  Thr  Ser  Trp  Tyr  Val
               115                      120                      125

Ala  Leu  Lys  Arg  Thr  Gly  Gln  Tyr  Lys  Leu  Gly  Ser  Lys  Thr  Gly  Pro
     130                      135                      140

Gly  Gln  Lys  Ala  Ile  Leu  Phe  Leu  Pro  Met  Ser  Ala  Lys  Ser
145                      150                      155
```

( 2 ) INFORMATION FOR SEQ ID NO:4:

( i ) SEQUENCE CHARACTERISTICS:
        ( A ) LENGTH: 351 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..348

( x i ) SEQUENCE DESCRIPTION: SEQ ID NO:4:

```
ATG  GAT  TAC  TAC  AGA  AAA  TAT  GCA  GCT  ATC  TTT  CTG  GTC  ACA  TTG  TCG        48
Met  Asp  Tyr  Tyr  Arg  Lys  Tyr  Ala  Ala  Ile  Phe  Leu  Val  Thr  Leu  Ser
160                      165                      170                      175

GTG  TTT  CTG  CAT  GTT  CTC  CAT  TCC  GCT  CCT  GAT  GTG  CAG  GAT  TGC  CCA        96
Val  Phe  Leu  His  Val  Leu  His  Ser  Ala  Pro  Asp  Val  Gln  Asp  Cys  Pro
               180                      185                      190

GAA  TGC  ACG  CTA  CAG  GAA  AAC  CCA  TTC  TTC  TCC  CAG  CCG  GGT  GCC  CCA       144
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Glu | Cys | Thr | Leu | Gln | Glu | Asn | Pro | Phe | Phe | Ser | Gln | Pro | Gly | Ala | Pro |     |
|     |     |     | 195 |     |     |     | 200 |     |     |     |     |     | 205 |     |     |     |
| ATA | CTT | CAG | TGC | ATG | GGC | TGC | TGC | TTC | TCT | AGA | GCA | TAT | CCC | ACT | CCA | 192 |
| Ile | Leu | Gln | Cys | Met | Gly | Cys | Cys | Phe | Ser | Arg | Ala | Tyr | Pro | Thr | Pro |     |
|     |     | 210 |     |     |     |     | 215 |     |     |     |     | 220 |     |     |     |     |
| CTA | AGG | TCC | AAG | AAG | ACG | ATG | TTG | GTC | CAA | AAG | AAC | GTC | ACC | TCA | GAG | 240 |
| Leu | Arg | Ser | Lys | Lys | Thr | Met | Leu | Val | Gln | Lys | Asn | Val | Thr | Ser | Glu |     |
|     | 225 |     |     |     |     | 230 |     |     |     |     | 235 |     |     |     |     |     |
| TCC | ACT | TGC | TGT | GTA | GCT | AAA | TCA | TAT | AAC | AGG | GTC | ACA | GTA | ATG | GGG | 288 |
| Ser | Thr | Cys | Cys | Val | Ala | Lys | Ser | Tyr | Asn | Arg | Val | Thr | Val | Met | Gly |     |
| 240 |     |     |     |     | 245 |     |     |     |     | 250 |     |     |     |     | 255 |     |
| GGT | TTC | AAA | GTG | GAG | AAC | CAC | ACG | GCG | TGC | CAC | TGC | AGT | ACT | TGT | TAT | 336 |
| Gly | Phe | Lys | Val | Glu | Asn | His | Thr | Ala | Cys | His | Cys | Ser | Thr | Cys | Tyr |     |
|     |     |     |     | 260 |     |     |     |     | 265 |     |     |     |     | 270 |     |     |
| TAT | CAC | AAA | TCT | TAA |     |     |     |     |     |     |     |     |     |     |     | 351 |
| Tyr | His | Lys | Ser |     |     |     |     |     |     |     |     |     |     |     |     |     |
|     |     |     | 275 |     |     |     |     |     |     |     |     |     |     |     |     |     |

(2) INFORMATION FOR SEQ ID NO:5:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:5:

|     |     |     |     |     |     |     |     |     |     |     |     |     |     |     |
|-----|-----|-----|-----|-----|-----|-----|-----|-----|-----|-----|-----|-----|-----|-----|
| Met | Asp | Tyr | Tyr | Arg | Lys | Tyr | Ala | Ala | Ile | Phe | Leu | Val | Thr | Leu | Ser |
| 1   |     |     |     | 5   |     |     |     |     | 10  |     |     |     |     | 15  |
| Val | Phe | Leu | His | Val | Leu | His | Ser | Ala | Pro | Asp | Val | Gln | Asp | Cys | Pro |
|     |     |     | 20  |     |     |     |     | 25  |     |     |     |     | 30  |     |
| Glu | Cys | Thr | Leu | Gln | Glu | Asn | Pro | Phe | Phe | Ser | Gln | Pro | Gly | Ala | Pro |
|     |     |     | 35  |     |     |     |     | 40  |     |     |     |     | 45  |     |
| Ile | Leu | Gln | Cys | Met | Gly | Cys | Cys | Phe | Ser | Arg | Ala | Tyr | Pro | Thr | Pro |
|     |     | 50  |     |     |     |     | 55  |     |     |     |     | 60  |     |     |
| Leu | Arg | Ser | Lys | Lys | Thr | Met | Leu | Val | Gln | Lys | Asn | Val | Thr | Ser | Glu |
| 65  |     |     |     |     | 70  |     |     |     |     | 75  |     |     |     |     | 80  |
| Ser | Thr | Cys | Cys | Val | Ala | Lys | Ser | Tyr | Asn | Arg | Val | Thr | Val | Met | Gly |
|     |     |     |     | 85  |     |     |     |     | 90  |     |     |     |     | 95  |
| Gly | Phe | Lys | Val | Glu | Asn | His | Thr | Ala | Cys | His | Cys | Ser | Thr | Cys | Tyr |
|     |     |     | 100 |     |     |     |     | 105 |     |     |     |     | 110 |     |
| Tyr | His | Lys | Ser |     |     |     |     |     |     |     |     |     |     |     |
|     |     |     | 115 |     |     |     |     |     |     |     |     |     |     |     |

(2) INFORMATION FOR SEQ ID NO:6:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..813

(xi) SEQUENCE DESCRIPTION: SEQ ID NO:6:

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| ATG | GCC | AAA | GTT | CCA | GAC | ATG | TTT | GAA | GAC | CTG | AAG | AAC | TGT | TAC | AGT | 48  |
| Met | Ala | Lys | Val | Pro | Asp | Met | Phe | Glu | Asp | Leu | Lys | Asn | Cys | Tyr | Ser |     |
|     |     | 120 |     |     |     |     | 125 |     |     |     |     | 130 |     |     |     |     |
| GAA | AAT | GAA | GAA | GAC | AGT | TCC | TCC | ATT | GAT | CAT | CTG | TCT | CTG | AAT | CAG | 96  |
| Glu | Asn | Glu | Glu | Asp | Ser | Ser | Ser | Ile | Asp | His | Leu | Ser | Leu | Asn | Gln |     |

|     |     |     |     | 135 |     |     |     |     | 140 |     |     |     |     | 145 |     |     |
|-----|-----|-----|-----|-----|-----|-----|-----|-----|-----|-----|-----|-----|-----|-----|-----|-----|
| AAA | TCC | TTC | TAT | CAT | GTA | AGC | TAT | GGC | CCA | CTC | CAT | GAA | GGC | TGC | ATG | 144 |
| Lys | Ser | Phe | Tyr | His | Val | Ser | Tyr | Gly | Pro | Leu | His | Glu | Gly | Cys | Met |     |
| 150 |     |     |     |     | 155 |     |     |     |     | 160 |     |     |     |     | 165 |     |
| GAT | CAA | TCT | GTG | TCT | CTG | AGT | ATC | TCT | GAA | ACC | TCT | AAA | ACA | TCC | AAG | 192 |
| Asp | Gln | Ser | Val | Ser | Leu | Ser | Ile | Ser | Glu | Thr | Ser | Lys | Thr | Ser | Lys |     |
|     |     |     |     | 170 |     |     |     |     | 175 |     |     |     |     | 180 |     |     |
| CTT | ACC | TTC | AAG | GAG | AGC | ATG | GTG | GTA | GTA | GCA | ACC | AAC | GGG | AAG | GTT | 240 |
| Leu | Thr | Phe | Lys | Glu | Ser | Met | Val | Val | Val | Ala | Thr | Asn | Gly | Lys | Val |     |
|     |     |     | 185 |     |     |     |     |     | 190 |     |     |     |     | 195 |     |     |
| CTG | AAG | AAG | AGA | CGG | TTG | AGT | TTA | AGC | CAA | TCC | ATC | ACT | GAT | GAT | GAC | 288 |
| Leu | Lys | Lys | Arg | Arg | Leu | Ser | Leu | Ser | Gln | Ser | Ile | Thr | Asp | Asp | Asp |     |
|     |     | 200 |     |     |     |     | 205 |     |     |     |     | 210 |     |     |     |     |
| CTG | GAG | GCC | ATC | GCC | AAT | GAC | TCA | GAG | GAA | GAA | ATC | ATC | AAG | CCT | AGG | 336 |
| Leu | Glu | Ala | Ile | Ala | Asn | Asp | Ser | Glu | Glu | Glu | Ile | Ile | Lys | Pro | Arg |     |
|     |     | 215 |     |     |     |     | 220 |     |     |     |     | 225 |     |     |     |     |
| TCA | GCA | CCT | TTT | AGC | TTC | CTG | AGC | AAT | GTG | AAA | TAC | AAC | TTT | ATG | AGG | 384 |
| Ser | Ala | Pro | Phe | Ser | Phe | Leu | Ser | Asn | Val | Lys | Tyr | Asn | Phe | Met | Arg |     |
| 230 |     |     |     |     | 235 |     |     |     |     | 240 |     |     |     |     | 245 |     |
| ATC | ATC | AAA | TAC | GAA | TTC | ATC | CTG | AAT | GAC | GCC | CTC | AAT | CAA | AGT | ATA | 432 |
| Ile | Ile | Lys | Tyr | Glu | Phe | Ile | Leu | Asn | Asp | Ala | Leu | Asn | Gln | Ser | Ile |     |
|     |     |     |     | 250 |     |     |     |     | 255 |     |     |     |     | 260 |     |     |
| ATT | CGA | GCC | AAT | GAT | CAG | TAC | CTC | ACG | GCT | GCT | GCA | TTA | CAT | AAT | CTG | 480 |
| Ile | Arg | Ala | Asn | Asp | Gln | Tyr | Leu | Thr | Ala | Ala | Ala | Leu | His | Asn | Leu |     |
|     |     |     |     | 265 |     |     |     |     | 270 |     |     |     |     | 275 |     |     |
| GAT | GAA | GCA | GTG | AAA | TTT | GAC | ATG | GGT | GCT | TAT | AAG | TCA | TCA | AAG | GAT | 528 |
| Asp | Glu | Ala | Val | Lys | Phe | Asp | Met | Gly | Ala | Tyr | Lys | Ser | Ser | Lys | Asp |     |
|     |     | 280 |     |     |     |     | 285 |     |     |     |     | 290 |     |     |     |     |
| GAT | GCT | AAA | ATT | ACC | GTG | ATT | CTA | AGA | ATC | TCA | AAA | ACT | CAA | TTG | TAT | 576 |
| Asp | Ala | Lys | Ile | Thr | Val | Ile | Leu | Arg | Ile | Ser | Lys | Thr | Gln | Leu | Tyr |     |
|     |     | 295 |     |     |     |     | 300 |     |     |     |     | 305 |     |     |     |     |
| GTG | ACT | GCC | CAA | GAT | GAA | GAC | CAA | CCA | GTG | CTG | CTG | AAG | GAG | ATG | CCT | 624 |
| Val | Thr | Ala | Gln | Asp | Glu | Asp | Gln | Pro | Val | Leu | Leu | Lys | Glu | Met | Pro |     |
| 310 |     |     |     |     | 315 |     |     |     |     | 320 |     |     |     |     | 325 |     |
| GAG | ATA | CCC | AAA | ACC | ATC | ACA | GGT | AGT | GAG | ACC | AAC | CTC | CTC | TTC | TTC | 672 |
| Glu | Ile | Pro | Lys | Thr | Ile | Thr | Gly | Ser | Glu | Thr | Asn | Leu | Leu | Phe | Phe |     |
|     |     |     |     | 330 |     |     |     |     | 335 |     |     |     |     | 340 |     |     |
| TGG | GAA | ACT | CAC | GGC | ACT | AAG | AAC | TAT | TTC | ACA | TCA | GTT | GCC | CAT | CCA | 720 |
| Trp | Glu | Thr | His | Gly | Thr | Lys | Asn | Tyr | Phe | Thr | Ser | Val | Ala | His | Pro |     |
|     |     |     | 345 |     |     |     |     |     | 350 |     |     |     |     | 355 |     |     |
| AAC | TTG | TTT | ATT | GCC | ACA | AAG | CAA | GAC | TAC | TGG | GTG | TGC | TTG | GCA | GGG | 768 |
| Asn | Leu | Phe | Ile | Ala | Thr | Lys | Gln | Asp | Tyr | Trp | Val | Cys | Leu | Ala | Gly |     |
|     |     | 360 |     |     |     |     | 365 |     |     |     |     | 370 |     |     |     |     |
| GGG | CCA | CCC | TCT | ATC | ACT | GAC | TTT | CAG | ATA | CTG | GAA | AAC | CAG | GCG | TAG | 816 |
| Gly | Pro | Pro | Ser | Ile | Thr | Asp | Phe | Gln | Ile | Leu | Glu | Asn | Gln | Ala |     |     |
|     | 375 |     |     |     |     | 380 |     |     |     |     | 385 |     |     |     |     |     |

( 2 ) INFORMATION FOR SEQ ID NO:7:

( i ) SEQUENCE CHARACTERISTICS:
        ( A ) LENGTH: 271 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Ala | Lys | Val | Pro | Asp | Met | Phe | Glu | Asp | Leu | Lys | Asn | Cys | Tyr | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Asn | Glu | Glu | Asp | Ser | Ser | Ser | Ile | Asp | His | Leu | Ser | Leu | Asn | Gln |
|     |     |     | 20  |     |     |     |     | 25  |     |     |     |     | 30  |     |     |

```
Lys  Ser  Phe  Tyr  His  Val  Ser  Tyr  Gly  Pro  Leu  His  Glu  Gly  Cys  Met
          35                  40                       45

Asp  Gln  Ser  Val  Ser  Leu  Ser  Ile  Ser  Glu  Thr  Ser  Lys  Thr  Ser  Lys
          50                  55                       60

Leu  Thr  Phe  Lys  Glu  Ser  Met  Val  Val  Val  Ala  Thr  Asn  Gly  Lys  Val
65                       70                  75                            80

Leu  Lys  Lys  Arg  Arg  Leu  Ser  Leu  Ser  Gln  Ser  Ile  Thr  Asp  Asp
                    85                       90                       95

Leu  Glu  Ala  Ile  Ala  Asn  Asp  Ser  Glu  Glu  Ile  Ile  Lys  Pro  Arg
                    100                  105                 110

Ser  Ala  Pro  Phe  Ser  Phe  Leu  Ser  Asn  Val  Lys  Tyr  Asn  Phe  Met  Arg
               115                  120                 125

Ile  Ile  Lys  Tyr  Glu  Phe  Ile  Leu  Asn  Asp  Ala  Leu  Asn  Gln  Ser  Ile
          130                  135                      140

Ile  Arg  Ala  Asn  Asp  Gln  Tyr  Leu  Thr  Ala  Ala  Ala  Leu  His  Asn  Leu
145                      150                      155                      160

Asp  Glu  Ala  Val  Lys  Phe  Asp  Met  Gly  Ala  Tyr  Lys  Ser  Ser  Lys  Asp
                    165                      170                      175

Asp  Ala  Lys  Ile  Thr  Val  Ile  Leu  Arg  Ile  Ser  Lys  Thr  Gln  Leu  Tyr
                    180                      185                 190

Val  Thr  Ala  Gln  Asp  Glu  Asp  Gln  Pro  Val  Leu  Leu  Lys  Glu  Met  Pro
               195                      200                 205

Glu  Ile  Pro  Lys  Thr  Ile  Thr  Gly  Ser  Glu  Thr  Asn  Leu  Leu  Phe  Phe
          210                      215                 220

Trp  Glu  Thr  His  Gly  Thr  Lys  Asn  Tyr  Phe  Thr  Ser  Val  Ala  His  Pro
225                           230                 235                      240

Asn  Leu  Phe  Ile  Ala  Thr  Lys  Gln  Asp  Tyr  Trp  Val  Cys  Leu  Ala  Gly
                    245                      250                      255

Gly  Pro  Pro  Ser  Ile  Thr  Asp  Phe  Gln  Ile  Leu  Glu  Asn  Gln  Ala
               260                      265                 270
```

( 2 ) INFORMATION FOR SEQ ID NO:8:

( i ) SEQUENCE CHARACTERISTICS:
        ( A ) LENGTH: 480 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..477

( x i ) SEQUENCE DESCRIPTION: SEQ ID NO:8:

```
TCA  GCA  CCT  TTT  AGC  TTC  CTG  AGC  AAT  GTG  AAA  TAC  AAC  TTT  ATG  AGG     48
Ser  Ala  Pro  Phe  Ser  Phe  Leu  Ser  Asn  Val  Lys  Tyr  Asn  Phe  Met  Arg
          275                      280                      285

ATC  ATC  AAA  TAC  GAA  TTC  ATC  CTG  AAT  GAC  GCC  CTC  AAT  CAA  AGT  ATA     96
Ile  Ile  Lys  Tyr  Glu  Phe  Ile  Leu  Asn  Asp  Ala  Leu  Asn  Gln  Ser  Ile
          290                      295                      300

ATT  CGA  GCC  AAT  GAT  CAG  TAC  CTC  ACG  GCT  GCT  GCA  TTA  CAT  AAT  CTG    144
Ile  Arg  Ala  Asn  Asp  Gln  Tyr  Leu  Thr  Ala  Ala  Ala  Leu  His  Asn  Leu
305                      310                      315                      320

GAT  GAA  GCA  GTG  AAA  TTT  GAC  ATG  GGT  GCT  TAT  AAG  TCA  TCA  AAG  GAT    192
Asp  Glu  Ala  Val  Lys  Phe  Asp  Met  Gly  Ala  Tyr  Lys  Ser  Ser  Lys  Asp
                    325                      330                      335

GAT  GCT  AAA  ATT  ACC  GTG  ATT  CTA  AGA  ATC  TCA  AAA  ACT  CAA  TTG  TAT    240
Asp  Ala  Lys  Ile  Thr  Val  Ile  Leu  Arg  Ile  Ser  Lys  Thr  Gln  Leu  Tyr
                    340                      345                      350
```

| | | | | | | | | | | | | | | | | |
|---|---|---|---|---|---|---|---|---|---|---|---|---|---|---|---|---|
| GTG | ACT | GCC | CAA | GAT | GAA | GAC | CAA | CCA | GTG | CTG | CTG | AAG | GAG | ATG | CCT | 288 |
| Val | Thr | Ala | Gln | Asp | Glu | Asp | Gln | Pro | Val | Leu | Leu | Lys | Glu | Met | Pro | |
| | | 355 | | | | 360 | | | | | | 365 | | | | |
| GAG | ATA | CCC | AAA | ACC | ATC | ACA | GGT | AGT | GAG | ACC | AAC | CTC | CTC | TTC | TTC | 336 |
| Glu | Ile | Pro | Lys | Thr | Ile | Thr | Gly | Ser | Glu | Thr | Asn | Leu | Leu | Phe | Phe | |
| 370 | | | | | | 375 | | | | 380 | | | | | | |
| TGG | GAA | ACT | CAC | GGC | ACT | AAG | AAC | TAT | TTC | ACA | TCA | GTT | GCC | CAT | CCA | 384 |
| Trp | Glu | Thr | His | Gly | Thr | Lys | Asn | Tyr | Phe | Thr | Ser | Val | Ala | His | Pro | |
| 385 | | | | | 390 | | | | | 395 | | | | | 400 | |
| AAC | TTG | TTT | ATT | GCC | ACA | AAG | CAA | GAC | TAC | TGG | GTG | TGC | TTG | GCA | GGG | 432 |
| Asn | Leu | Phe | Ile | Ala | Thr | Lys | Gln | Asp | Tyr | Trp | Val | Cys | Leu | Ala | Gly | |
| | | | | 405 | | | | | 410 | | | | | 415 | | |
| GGG | CCA | CCC | TCT | ATC | ACT | GAC | TTT | CAG | ATA | CTG | GAA | AAC | CAG | GCG | TAG | 480 |
| Gly | Pro | Pro | Ser | Ile | Thr | Asp | Phe | Gln | Ile | Leu | Glu | Asn | Gln | Ala | | |
| | | | 420 | | | | | 425 | | | | | 430 | | | |

( 2 ) INFORMATION FOR SEQ ID NO:9:

( i ) SEQUENCE CHARACTERISTICS:
        ( A ) LENGTH: 159 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Ser | Ala | Pro | Phe | Ser | Phe | Leu | Ser | Asn | Val | Lys | Tyr | Asn | Phe | Met | Arg |
| 1 | | | | 5 | | | | | 10 | | | | | 15 | |
| Ile | Ile | Lys | Tyr | Glu | Phe | Ile | Leu | Asn | Asp | Ala | Leu | Asn | Gln | Ser | Ile |
| | | | 20 | | | | | 25 | | | | | 30 | | |
| Ile | Arg | Ala | Asn | Asp | Gln | Tyr | Leu | Thr | Ala | Ala | Ala | Leu | His | Asn | Leu |
| | | 35 | | | | | 40 | | | | | 45 | | | |
| Asp | Glu | Ala | Val | Lys | Phe | Asp | Met | Gly | Ala | Tyr | Lys | Ser | Ser | Lys | Asp |
| | 50 | | | | | 55 | | | | | 60 | | | | |
| Asp | Ala | Lys | Ile | Thr | Val | Ile | Leu | Arg | Ile | Ser | Lys | Thr | Gln | Leu | Tyr |
| 65 | | | | | 70 | | | | | 75 | | | | | 80 |
| Val | Thr | Ala | Gln | Asp | Glu | Asp | Gln | Pro | Val | Leu | Leu | Lys | Glu | Met | Pro |
| | | | | 85 | | | | | 90 | | | | | 95 | |
| Glu | Ile | Pro | Lys | Thr | Ile | Thr | Gly | Ser | Glu | Thr | Asn | Leu | Leu | Phe | Phe |
| | | | 100 | | | | | 105 | | | | | 110 | | |
| Trp | Glu | Thr | His | Gly | Thr | Lys | Asn | Tyr | Phe | Thr | Ser | Val | Ala | His | Pro |
| | | 115 | | | | | 120 | | | | | 125 | | | |
| Asn | Leu | Phe | Ile | Ala | Thr | Lys | Gln | Asp | Tyr | Trp | Val | Cys | Leu | Ala | Gly |
| | | 130 | | | | | 135 | | | | | 140 | | | |
| Gly | Pro | Pro | Ser | Ile | Thr | Asp | Phe | Gln | Ile | Leu | Glu | Asn | Gln | Ala | |
| 145 | | | | | 150 | | | | | 155 | | | | | |

( 2 ) INFORMATION FOR SEQ ID NO:10:

( i ) SEQUENCE CHARACTERISTICS:
        ( A ) LENGTH: 810 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..807

( x i ) SEQUENCE DESCRIPTION: SEQ ID NO:10:

| | | | | | | | | | | | | | | | | |
|---|---|---|---|---|---|---|---|---|---|---|---|---|---|---|---|---|
| ATG | GCA | GAA | GTA | CCT | GAG | CTC | GCC | AGT | GAA | ATG | ATG | GCT | TAT | TAC | AGT | 48 |
| Met | Ala | Glu | Val | Pro | Glu | Leu | Ala | Ser | Glu | Met | Met | Ala | Tyr | Tyr | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| GGC | AAT | GAG | GAT | GAC | TTG | TTC | TTT | GAA | GCT | GAT | GGC | CCT | AAA | CAG | ATG | 96 |
| Gly | Asn | Glu | Asp | Asp | Leu | Phe | Phe | Glu | Ala | Asp | Gly | Pro | Lys | Gln | Met | |
| | | | 180 | | | | | 185 | | | | | 190 | | | |
| AAG | TGC | TCC | TTC | CAG | GAC | CTG | GAC | CTC | TGC | CCT | CTG | GAT | GGC | GGC | ATC | 144 |
| Lys | Cys | Ser | Phe | Gln | Asp | Leu | Asp | Leu | Cys | Pro | Leu | Asp | Gly | Gly | Ile | |
| | | 195 | | | | | 200 | | | | | 205 | | | | |
| CAG | CTA | CGA | ATC | TCC | GAC | CAC | CAC | TAC | AGC | AAG | GGC | TTC | AGG | CAG | GCC | 192 |
| Gln | Leu | Arg | Ile | Ser | Asp | His | His | Tyr | Ser | Lys | Gly | Phe | Arg | Gln | Ala | |
| 210 | | | | | | 215 | | | | | 220 | | | | | |
| GCG | TCA | GTT | GTT | GTG | GCC | ATG | GAC | AAG | CTG | AGG | AAG | ATG | CTG | GTT | CCC | 240 |
| Ala | Ser | Val | Val | Val | Ala | Met | Asp | Lys | Leu | Arg | Lys | Met | Leu | Val | Pro | |
| 225 | | | | | 230 | | | | | 235 | | | | | 240 | |
| TGC | CCA | CAG | ACC | TTC | CAG | GAG | AAT | GAC | CTG | AGC | ACC | TTC | TTT | CCC | TTC | 288 |
| Cys | Pro | Gln | Thr | Phe | Gln | Glu | Asn | Asp | Leu | Ser | Thr | Phe | Phe | Pro | Phe | |
| | | | | 245 | | | | | 250 | | | | | 255 | | |
| ATC | TTT | GAA | GAA | GAA | CCT | ATC | TTC | TTT | GAC | ACA | TGG | GAT | AAC | GAG | GCT | 336 |
| Ile | Phe | Glu | Glu | Glu | Pro | Ile | Phe | Phe | Asp | Thr | Trp | Asp | Asn | Glu | Ala | |
| | | | 260 | | | | | 265 | | | | | 270 | | | |
| TAT | GTG | CAC | GAT | GCA | CCT | GTA | CGA | TCA | CTG | AAC | TGC | ACG | CTC | CGG | GAC | 384 |
| Tyr | Val | His | Asp | Ala | Pro | Val | Arg | Ser | Leu | Asn | Cys | Thr | Leu | Arg | Asp | |
| | | 275 | | | | | 280 | | | | | 285 | | | | |
| TCA | CAG | CAA | AAA | AGC | TTG | GTG | ATG | TCT | GGT | CCA | TAT | GAA | CTG | AAA | GCT | 432 |
| Ser | Gln | Gln | Lys | Ser | Leu | Val | Met | Ser | Gly | Pro | Tyr | Glu | Leu | Lys | Ala | |
| 290 | | | | | 295 | | | | | 300 | | | | | | |
| CTC | CAC | CTC | CAG | GGA | CAG | GAT | ATG | GAG | CAA | CAA | GTG | GTG | TTC | TCC | ATG | 480 |
| Leu | His | Leu | Gln | Gly | Gln | Asp | Met | Glu | Gln | Gln | Val | Val | Phe | Ser | Met | |
| 305 | | | | | 310 | | | | | 315 | | | | | 320 | |
| TCC | TTT | GTA | CAA | GGA | GAA | GAA | AGT | AAT | GAC | AAA | ATA | CCT | GTG | GCC | TTG | 528 |
| Ser | Phe | Val | Gln | Gly | Glu | Glu | Ser | Asn | Asp | Lys | Ile | Pro | Val | Ala | Leu | |
| | | | | 325 | | | | | 330 | | | | | 335 | | |
| GGC | CTC | AAG | GAA | AAG | AAT | CTG | TAC | CTG | TCC | TGC | GTG | TTG | AAA | GAT | GAT | 576 |
| Gly | Leu | Lys | Glu | Lys | Asn | Leu | Tyr | Leu | Ser | Cys | Val | Leu | Lys | Asp | Asp | |
| | | | 340 | | | | | 345 | | | | | 350 | | | |
| AAG | CCC | ACT | CTA | CAG | CTG | GAG | AGT | GTA | GAT | CCC | AAA | AAT | TAC | CCA | AAG | 624 |
| Lys | Pro | Thr | Leu | Gln | Leu | Glu | Ser | Val | Asp | Pro | Lys | Asn | Tyr | Pro | Lys | |
| | | | 355 | | | | | 360 | | | | | 365 | | | |
| AAG | AAG | ATG | GAA | AAG | CGA | TTT | GTC | TTC | AAC | AAG | ATA | GAA | ATC | AAT | AAC | 672 |
| Lys | Lys | Met | Glu | Lys | Arg | Phe | Val | Phe | Asn | Lys | Ile | Glu | Ile | Asn | Asn | |
| | 370 | | | | | 375 | | | | | 380 | | | | | |
| AAG | CTG | GAA | TTT | GAG | TCT | GCC | CAG | TTC | CCC | AAC | TGG | TAC | ATC | AGC | ACC | 720 |
| Lys | Leu | Glu | Phe | Glu | Ser | Ala | Gln | Phe | Pro | Asn | Trp | Tyr | Ile | Ser | Thr | |
| 385 | | | | | 390 | | | | | 395 | | | | | 400 | |
| TCT | CAA | GCA | GAA | AAC | ATG | CCC | GTC | TTC | CTG | GGA | GGG | ACC | AAA | GGC | GGC | 768 |
| Ser | Gln | Ala | Glu | Asn | Met | Pro | Val | Phe | Leu | Gly | Gly | Thr | Lys | Gly | Gly | |
| | | | | 405 | | | | | 410 | | | | | 415 | | |
| CAG | GAT | ATA | ACT | GAC | TTC | ACC | ATG | CAA | TTT | GTG | TCT | TCC | TAA | | | 810 |
| Gln | Asp | Ile | Thr | Asp | Phe | Thr | Met | Gln | Phe | Val | Ser | Ser | | | | |
| | | | 420 | | | | | 425 | | | | | | | | |

( 2 ) INFORMATION FOR SEQ ID NO:11:

( i ) SEQUENCE CHARACTERISTICS:
        ( A ) LENGTH: 269 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Ala | Glu | Val | Pro | Glu | Leu | Ala | Ser | Glu | Met | Met | Ala | Tyr | Tyr | Ser |
| 1 | | | | 5 | | | | | 10 | | | | | 15 | |

```
Gly  Asn  Glu  Asp  Asp  Leu  Phe  Phe  Glu  Ala  Asp  Gly  Pro  Lys  Gln  Met
               20                  25                       30

Lys  Cys  Ser  Phe  Gln  Asp  Leu  Asp  Leu  Cys  Pro  Leu  Asp  Gly  Gly  Ile
               35                  40                       45

Gln  Leu  Arg  Ile  Ser  Asp  His  His  Tyr  Ser  Lys  Gly  Phe  Arg  Gln  Ala
      50                       55                       60

Ala  Ser  Val  Val  Val  Ala  Met  Asp  Lys  Leu  Arg  Lys  Met  Leu  Val  Pro
 65                       70                       75                       80

Cys  Pro  Gln  Thr  Phe  Gln  Glu  Asn  Asp  Leu  Ser  Thr  Phe  Phe  Pro  Phe
                    85                       90                       95

Ile  Phe  Glu  Glu  Glu  Pro  Ile  Phe  Phe  Asp  Thr  Trp  Asp  Asn  Glu  Ala
               100                      105                      110

Tyr  Val  His  Asp  Ala  Pro  Val  Arg  Ser  Leu  Asn  Cys  Thr  Leu  Arg  Asp
          115                      120                      125

Ser  Gln  Gln  Lys  Ser  Leu  Val  Met  Ser  Gly  Pro  Tyr  Glu  Leu  Lys  Ala
     130                      135                      140

Leu  His  Leu  Gln  Gly  Gln  Asp  Met  Glu  Gln  Gln  Val  Val  Phe  Ser  Met
145                      150                      155                      160

Ser  Phe  Val  Gln  Gly  Glu  Glu  Ser  Asn  Asp  Lys  Ile  Pro  Val  Ala  Leu
                    165                      170                      175

Gly  Leu  Lys  Glu  Lys  Asn  Leu  Tyr  Leu  Ser  Cys  Val  Leu  Lys  Asp  Asp
               180                      185                      190

Lys  Pro  Thr  Leu  Gln  Leu  Glu  Ser  Val  Asp  Pro  Lys  Asn  Tyr  Pro  Lys
          195                      200                      205

Lys  Lys  Met  Glu  Lys  Arg  Phe  Val  Phe  Asn  Lys  Ile  Glu  Ile  Asn  Asn
     210                      215                      220

Lys  Leu  Glu  Phe  Glu  Ser  Ala  Gln  Phe  Pro  Asn  Trp  Tyr  Ile  Ser  Thr
225                      230                      235                      240

Ser  Gln  Ala  Glu  Asn  Met  Pro  Val  Phe  Leu  Gly  Gly  Thr  Lys  Gly  Gly
                    245                      250                      255

Gln  Asp  Ile  Thr  Asp  Phe  Thr  Met  Gln  Phe  Val  Ser  Ser
                    260                      265
```

(2) INFORMATION FOR SEQ ID NO:12:

(i) SEQUENCE CHARACTERISTICS:
      (A) LENGTH: 462 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..459

(xi) SEQUENCE DESCRIPTION: SEQ ID NO:12:

```
GCA  CCT  GTA  CGA  TCA  CTG  AAC  TGC  ACG  CTC  CGG  GAC  TCA  CAG  CAA  AAA        48
Ala  Pro  Val  Arg  Ser  Leu  Asn  Cys  Thr  Leu  Arg  Asp  Ser  Gln  Gln  Lys
               275                      280                      285

AGC  TTG  GTG  ATG  TCT  GGT  CCA  TAT  GAA  CTG  AAA  GCT  CTC  CAC  CTC  CAG        96
Ser  Leu  Val  Met  Ser  Gly  Pro  Tyr  Glu  Leu  Lys  Ala  Leu  His  Leu  Gln
               290                      295                      300

GGA  CAG  GAT  ATG  GAG  CAA  CAA  GTG  GTG  TTC  TCC  ATG  TCC  TTT  GTA  CAA       144
Gly  Gln  Asp  Met  Glu  Gln  Gln  Val  Val  Phe  Ser  Met  Ser  Phe  Val  Gln
               305                      310                      315

GGA  GAA  GAA  AGT  AAT  GAC  AAA  ATA  CCT  GTG  GCC  TTG  GGC  CTC  AAG  GAA       192
Gly  Glu  Glu  Ser  Asn  Asp  Lys  Ile  Pro  Val  Ala  Leu  Gly  Leu  Lys  Glu
     320                      325                      330

AAG  AAT  CTG  TAC  CTG  TCC  TGC  GTG  TTG  AAA  GAT  GAT  AAG  CCC  ACT  CTA       240
```

| | | | | | | | | | | | | | | | |
|---|---|---|---|---|---|---|---|---|---|---|---|---|---|---|---|
| Lys | Asn | Leu | Tyr | Leu | Ser | Cys | Val | Leu | Lys | Asp | Asp | Lys | Pro | Thr | Leu |
| 335 | | | | | 340 | | | | 345 | | | | | | 350 |

| | | | | | | | | | | | | | | | |
|---|---|---|---|---|---|---|---|---|---|---|---|---|---|---|---|
| CAG | CTG | GAG | AGT | GTA | GAT | CCC | AAA | AAT | TAC | CCA | AAG | AAG | AAG | ATG | GAA |
| Gln | Leu | Glu | Ser | Val | Asp | Pro | Lys | Asn | Tyr | Pro | Lys | Lys | Lys | Met | Glu |
| | | | | 355 | | | | | 360 | | | | | 365 | |

288

| AAG | CGA | TTT | GTC | TTC | AAC | AAG | ATA | GAA | ATC | AAT | AAC | AAG | CTG | GAA | TTT |
|---|---|---|---|---|---|---|---|---|---|---|---|---|---|---|---|
| Lys | Arg | Phe | Val | Phe | Asn | Lys | Ile | Glu | Ile | Asn | Asn | Lys | Leu | Glu | Phe |
| | | | 370 | | | | | 375 | | | | | 380 | | |

336

| GAG | TCT | GCC | CAG | TTC | CCC | AAC | TGG | TAC | ATC | AGC | ACC | TCT | CAA | GCA | GAA |
|---|---|---|---|---|---|---|---|---|---|---|---|---|---|---|---|
| Glu | Ser | Ala | Gln | Phe | Pro | Asn | Trp | Tyr | Ile | Ser | Thr | Ser | Gln | Ala | Glu |
| | | 385 | | | | | 390 | | | | | 395 | | | |

384

| AAC | ATG | CCC | GTC | TTC | CTG | GGA | GGG | ACC | AAA | GGC | GGC | CAG | GAT | ATA | ACT |
|---|---|---|---|---|---|---|---|---|---|---|---|---|---|---|---|
| Asn | Met | Pro | Val | Phe | Leu | Gly | Gly | Thr | Lys | Gly | Gly | Gln | Asp | Ile | Thr |
| | 400 | | | | | 405 | | | | 410 | | | | | |

432

| GAC | TTC | ACC | ATG | CAA | TTT | GTG | TCT | TCC | TAA |
|---|---|---|---|---|---|---|---|---|---|
| Asp | Phe | Thr | Met | Gln | Phe | Val | Ser | Ser | |
| 415 | | | | | 420 | | | | |

462

( 2 ) INFORMATION FOR SEQ ID NO:13:

( i ) SEQUENCE CHARACTERISTICS:
        ( A ) LENGTH: 153 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Ala | Pro | Val | Arg | Ser | Leu | Asn | Cys | Thr | Leu | Arg | Asp | Ser | Gln | Gln | Lys |
|---|---|---|---|---|---|---|---|---|---|---|---|---|---|---|---|
| 1 | | | | 5 | | | | | 10 | | | | | 15 | |

| Ser | Leu | Val | Met | Ser | Gly | Pro | Tyr | Glu | Leu | Lys | Ala | Leu | His | Leu | Gln |
|---|---|---|---|---|---|---|---|---|---|---|---|---|---|---|---|
| | | | 20 | | | | | 25 | | | | | 30 | | |

| Gly | Gln | Asp | Met | Glu | Gln | Gln | Val | Val | Phe | Ser | Met | Ser | Phe | Val | Gln |
|---|---|---|---|---|---|---|---|---|---|---|---|---|---|---|---|
| | | 35 | | | | | 40 | | | | | 45 | | | |

| Gly | Glu | Glu | Ser | Asn | Asp | Lys | Ile | Pro | Val | Ala | Leu | Gly | Leu | Lys | Glu |
|---|---|---|---|---|---|---|---|---|---|---|---|---|---|---|---|
| | 50 | | | | | 55 | | | | | 60 | | | | |

| Lys | Asn | Leu | Tyr | Leu | Ser | Cys | Val | Leu | Lys | Asp | Asp | Lys | Pro | Thr | Leu |
|---|---|---|---|---|---|---|---|---|---|---|---|---|---|---|---|
| 65 | | | | | 70 | | | | 75 | | | | | | 80 |

| Gln | Leu | Glu | Ser | Val | Asp | Pro | Lys | Asn | Tyr | Pro | Lys | Lys | Lys | Met | Glu |
|---|---|---|---|---|---|---|---|---|---|---|---|---|---|---|---|
| | | | | 85 | | | | | 90 | | | | | 95 | |

| Lys | Arg | Phe | Val | Phe | Asn | Lys | Ile | Glu | Ile | Asn | Asn | Lys | Leu | Glu | Phe |
|---|---|---|---|---|---|---|---|---|---|---|---|---|---|---|---|
| | | | 100 | | | | | 105 | | | | | 110 | | |

| Glu | Ser | Ala | Gln | Phe | Pro | Asn | Trp | Tyr | Ile | Ser | Thr | Ser | Gln | Ala | Glu |
|---|---|---|---|---|---|---|---|---|---|---|---|---|---|---|---|
| | | 115 | | | | | 120 | | | | | 125 | | | |

| Asn | Met | Pro | Val | Phe | Leu | Gly | Gly | Thr | Lys | Gly | Gly | Gln | Asp | Ile | Thr |
|---|---|---|---|---|---|---|---|---|---|---|---|---|---|---|---|
| | 130 | | | | | 135 | | | | 140 | | | | | |

| Asp | Phe | Thr | Met | Gln | Phe | Val | Ser | Ser |
|---|---|---|---|---|---|---|---|---|
| 145 | | | | | 150 | | | |